(12) United States Patent
Lodie et al.

(10) Patent No.: US 8,481,022 B2
(45) Date of Patent: Jul. 9, 2013

(54) METHOD OF TREATING AUTOIMMUNE DISEASE WITH MESENCHYMAL STEM CELLS

(75) Inventors: Tracey Lodie, Sutton, MA (US); Michele Youd, Lexington, MA (US); Ross Tubo, Quincy, MA (US); Scott Eisenbeis, Westborough, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 13/193,469

(22) Filed: Jul. 28, 2011

(65) Prior Publication Data

US 2012/0121611 A1 May 17, 2012

Related U.S. Application Data

(63) Continuation of application No. 12/188,922, filed on Aug. 8, 2008, now abandoned.

(60) Provisional application No. 60/954,973, filed on Aug. 9, 2007.

(51) Int. Cl.
*A61K 48/00* (2006.01)
*A61K 39/00* (2006.01)
*A61K 38/00* (2006.01)

(52) U.S. Cl.
USPC .................. 424/93.1; 424/93.21; 424/144.1; 424/184.1

(58) Field of Classification Search
None
See application file for complete search history.

(56) References Cited

U.S. PATENT DOCUMENTS

| | | | |
|---|---|---|---|
| 4,810,643 A | 3/1989 | Souza | |
| 4,904,584 A | 2/1990 | Shaw | |
| 5,104,651 A | 4/1992 | Boone et al. | |
| 5,116,753 A | 5/1992 | Beattie et al. | |
| 5,214,132 A | 5/1993 | Kuga et al. | |
| 5,218,092 A | 6/1993 | Sasaki et al. | |
| 5,362,853 A | 11/1994 | Kuga et al. | |
| 5,574,008 A | 11/1996 | Johnson et al. | |
| 5,606,024 A | 2/1997 | Boone et al. | |
| 5,624,895 A | 4/1997 | Sobel | |
| 5,824,778 A | 10/1998 | Ishikawa et al. | |
| 5,824,784 A | 10/1998 | Kinstler et al. | |
| 6,017,876 A | 1/2000 | Gegg et al. | |
| 6,166,183 A | 12/2000 | Ishikawa et al. | |
| 6,261,550 B1 | 7/2001 | Osslund | |
| 6,534,272 B2 | 3/2003 | Polychronakos et al. | |
| 6,797,269 B2 | 9/2004 | Mosca et al. | |
| 7,220,407 B2 | 5/2007 | Mehta et al. | |
| 7,871,605 B2 * | 1/2011 | Hampson et al. | 424/93.7 |
| 2002/0044923 A1 | 4/2002 | Mosca et al. | |
| 2003/0064922 A1 | 4/2003 | Nissen et al. | |
| 2004/0209801 A1 | 10/2004 | Brand et al. | |
| 2006/0153894 A1 | 7/2006 | Ghabrial et al. | |
| 2006/0189520 A1 | 8/2006 | Brand et al. | |
| 2006/0281174 A1 | 12/2006 | Xu et al. | |
| 2010/0322894 A1 | 12/2010 | Atkinson et al. | |

FOREIGN PATENT DOCUMENTS

| | | |
|---|---|---|
| AU | 76380/91 | 11/1991 |
| AU | 10948/92 | 8/1992 |
| EP | 0243153 | 10/1987 |
| EP | 0256843 | 2/1988 |
| EP | 0272703 | 6/1988 |
| EP | 0335423 | 10/1989 |
| EP | 0401384 | 12/1990 |
| EP | 0459630 | 12/1991 |
| WO | WO 90/12874 | 11/1990 |
| WO | WO 2004/056875 A1 | 7/2004 |
| WO | WO 2005/086860 A2 | 9/2005 |
| WO | WO 2005/093044 A1 | 10/2005 |
| WO | WO 2006/094286 A2 | 9/2006 |
| WO | WO 2007/041368 | 4/2007 |
| WO | WO 2007/064757 | 6/2007 |
| WO | WO 2007/127408 A2 | 11/2007 |

OTHER PUBLICATIONS

Augello et al., Eur J Immunol, 35 (2005) pp. 1482-1490.*
Zorina et al., (Stem Cells, 2003; 21(4):377-388).*
Abdi et al., Diabetes. Jul. 2008; 57(7): 1759-1767.*
"Evaluating an Immunomodulatory Cell Therapy Product for Type 1 Diabetes" *Medical News Today* [online] (Oct. 26, 2007). Retrieved from the Internet: http://www.medicalnewstoday.com/articles/86807.php>.
Ansari, M.J.I. et al. "The programmed death-1 (PD-1) pathway regulates autoimmune diabetes in nonobese diabetic (NOD) mice" *J. Exp. Med.* 198(1):63-69 (2003).
Augello, A. et al. "Cell Therapy Using Allogeneic Bone Marrow Mesenchymal Stem Cells Prevents Tissue Damage in Collagen-Induced Arthritis" *Arthritis Rheum* 56(4):1175-1186 (2007).
Augello, A. et al. "Bone marrow mesenchymal progenitor cells inhibit lymphocyte proliferation by activation of the programmed death 1 pathway" *Eur. J. Immunol.* 35(5):1482-1490 (2005).
Banerjee et al., "Reversal of experimental diabetes by multiple bone marrow transplantation," *Biochemical and Biophysical Research Communications*, 328(1): 318-325 (2005).
Blank, C. et al. "Absence of Programmed Death Receptor 1 Alters Thymic Development and Enhances Generation of CD4/CD8 Double-Negative TCR-Transgenic T Cells" *J. Immunol.* 171:4574-4581 (2003).
Dean et al. "Graft-versus-host Disease: Emerging Concepts in Prevention and Therapy" *Curr. Hematol. Rep.* 2:287-294 (2003).
Ezquer, F.E. et al. "Systemic Administration of Multipotent Mesenchymal Stromal Cells Reverts Hyperglycemia and Prevents Nephropathy in Type 1 Diabetic Mice" *Biol. Blood Marrow Transplant.* 14:631-640 (2008).
Glennie, S. et al. "Bone marrow mesenchymal stem cells induce division arrest anergy of activated T cells" *Blood* 105:2821-2827 (2005) (published online Dec. 9, 2004).
Greenwald, R.J. et al. "The B7 Family Revisited" *Ann. Rev. Immunol.* 23:515-548 (2005).
Harrison, L.C. "The Prospect of Vaccination to Prevent Type 1 Diabetes" *Human Vaccines* 1(4):143-150 (Jul./Aug. 2005).

(Continued)

*Primary Examiner* — Daniel C Gamett
(74) *Attorney, Agent, or Firm* — Finnegan, Henderson, Farabow, Garrett & Dunner, LLP

(57) ABSTRACT

Methods and compositions for treating an autoimmune disease, such as new onset type 1 diabetes (T1D) in a subject using autologous or allogeneic mesenchymal stem cells administered to the subject prior to autoimmune-induced complete depletion of insulin-producing pancreatic beta cells, e.g., within six months of new onset type 1 diabetes (T1D) diagnosis or prior to the onset of disease in a subject determined to be at high risk for T1D.

22 Claims, 22 Drawing Sheets

OTHER PUBLICATIONS

Herold, K.C. et al. "Anti-CD3 Monoclonal Antibody in New-Onset Type 1 Diabetes Mellitus" *N. Engl. J. Med.* 346(22):1692-1698 (2002).

Ishida, M. et al. "Differential expression of PD-L1 and PD-L2, ligands for an inhibitory receptor PD-1, in the cells of lymphohematopoietic tissues" *Immunol. Lett.* 84:57-62 (2002).

Iwai, Y. et al. "PD-1 Inhibits Antiviral Immunity at the Effector Phase in the Liver" *J. Exp. Med.* 198(1):39-50 (2003).

Jones, S. et al. "The antiproliferative effect of mesenchymal stem cells is a fundamental property shared by all stromal cells" *J. Immunol.* 179:2824-2831 (2007).

Kang et al., "Hematopoietic stem cell transplantation prevents diabetes in NOD mice but does not contribute to significant islet cell regeneration once disease is established," *Exp Hematology*, 33:699-705 (2005).

Keymeulen, B. et al. "Insulin Needs after CD3-Antibody Therapy in New-Onset Type 1 Diabetes" *N. Engl. J. Med.* 352:2598-2608 (2005).

Latchman, Y.E. et al. "PD-L1-deficient mice show that PD-L1 on T cells, antigen-presenting cells, and host tissues negatively regulates T cells" *PNAS* 101(29):10691-10696 (2004).

Liang, S.C. et al. "Regulation of PD-1, PD-L1, and PD-L2 expression during normal and autoimmune responses" *Eur. J. Immunol.* 33:2706-2716 (2003).

Lee, R.H. et al. "Multipotent stromal cells from human marrow home to and promote repair of pancreatic islets and renal glomeruli in diabetic NOD/scid mice" *PNAS* 103(46):17438-17443 (2006).

Nishimura, H. et al. "Facilitation of β Selection and Modification of Positive Selection in the Thymus of PD-1-deficient Mice" *J. Exp. Med.* 191(5):891-897 (2000).

Nishimura, H. et al. "Immunological studies on PD-1-deficient mice: implication of PD-1 as a negative regulator for B cell responses" *Int. Immunol.* 10(10):1563-1572 (1998).

Nishimura, H et al. "Development of Lupus-like Autoimmune Diseases by Disruption of the PD-1 Gene Encoding an ITIM Motif-Carrying Immunoreceptor" *Immunity* 11:141-151 (1999).

Nishimura, H et al. "Autoimmune Dilated Cardiomyopathy in PD-1 Receptor-Deficient Mice" *Science* 291(5502):319-322 (2001).

Petroff, M.G. et al. "B7 Family Molecules Are Favorably Positioned at the Human Maternal-Fetal Interface" *Biol. Reprod.* 68:1496-1504 (2003).

Rasmusson, I. et al. "Mesenchymal stem cells inhibit lymphocyte proliferation by mitogens and alloantigens by different mechanisms" *Exp. Cell Res.* 305:33-41 (2005).

Ren, G. et al. "Mesencymal stem cell-mediated immunosuppression occurs via concerted action of chemokines and nitric oxide" *Cell Stem Cell* 2(2):141-150 (2008).

Ringdén, O. et al. "Mesenchymal stem cells for treatment of therapy-resistant graft-versus-host disease" *Transplantation* 81(10):1390-1397 (2006).

Rodig, N. et al. "Endothelial expression of PD-L1 and PD-L2 down-regulates $CD8^+$ T cell activation and cytolysis" *Eur. J. Immunol* 33:3117-3126 (2003).

Shlapatska, L.M. et al. "CD150 Association with Either the SH2-Containing Inositol Phosphatase or the SH2-Containing Protein Tyrosine Phosphatase Is Regulated by the Adaptor Protein SH2D1A" *J. Immunol.* 166:5480-5487 (2001).

Van Laar, J.M. et al. "Adult stem cells in the treatment of autoimmune diseases". *Rheumatology* 45:1187-1193 (2006) (Advance Access publication Jun. 15, 2006)

Wiendl, H. et al. "Muscle fibres and cultured muscle cells express the B7.1/2-related inducible co-stimulatory molecule, ICOSL: implications for the pathogenesis of inflammatory myopathies" *Brain* 126:1026-1035 (2003).

Xu, J. et al. "Reversal of Diabetes in Mice by Intrahepatic Injection of Bone-derived GFP-Murine Mesenchymal Stem Cells Infected with the Recombinant Retrovirus-carrying Human Insulin Gene" *World J. Surg.* 31:1872-1882 (2007).

Xu, J. et al. "Prevention of endotoxin-induced systemic response by bone marrow-derived mesenchymal stem cells in mice" *Am. J. Physiol. Lung Cell Mol. Physiol.* 293:L131-L141 (2007).

Yadav, D. et al. "Costimulation and Pancreatic Autoimmunity: The PD-1/PD-L Conundrum" *Rev. Diab. Stud.* 3:6-10 (2006).

International Search Report issued in International Application No. PCT/US2008/072630, dated Mar. 19, 2009.

Office Action mailed May 20, 2010 in U.S. Appl. No. 12/188,922.

Amendment filed Nov. 19, 2010 in U.S. Appl. No. 12/188,922.

Final Office Action mailed Jan. 31, 2011 in U.S. Appl. No. 12/188,922.

Bacigalupo, A., "Antithymocyte globulin for prevention of graft-versus-host disease," *Curr Opin Hematol.*, 2005, pp. 457-462, vol. 12.

Bevans et al., "Management of patients receiving antithymocyte globulin for aplastic anemia and myelodysplastic syndrome," *Clin J Oncol Nurs.*, 2004, pp. 377-382, vol. 8.

Kuga et al., "Mutagenesis of human granulocyte colony stimulating factor," *Biochem. Biophys. Res. Comm.*, 1989, pp. 103-111, vol. 159.

Lu et al., "Disulfide and secondary structures of recombinant human granulocyte colony stimulating factor," *Arch. Biochem. Biophys.*, 1989, pp. 81-92, vol. 268.

Nashan, B., "Antibody induction therapy in renal transplant patients receiving calcineurin-inhibitor immunosuppressive regimens: a comparative review," *BioDrugs*, 2005, pp. 39-46, vol. 19.

Smith et al., "Current immunosuppressive agents: efficacy, side effects, and utilization," *Pediatr Clin North Am*, 2003, pp. 1283-1300, vol. 50.

Restriction Requirement mailed Jul. 9, 2012 for U.S. Appl. No. 12/680,614.

Preliminary Amendment and Election under 35 U.S.C. § 121 dated Aug. 8, 2012, for U.S. Appl. No. 12/680,614.

Office Action mailed Sep. 18, 2012 for U.S. Appl. No. 12/680,614.

Amendment under 37 C.F.R. § 1.111 filed Feb. 19, 2013, for U.S. Appl. No. 12/680,614.

Declaration of Mark A. Atkinson, Ph.D. under 37 C.F.R. § 1.132 filed Feb. 19, 2013, for U.S. Appl. No. 12/680,614.

\* cited by examiner

| Genes differentially expressed in NOD MSCs |
|---|
| PD-L1 (−) |
| CXCL10/IP-10 (↑) |
| CXCL19 (↑) |
| CCL17 (↑) |
| Granzymes (↑) |
| TGFb2 (↑) |
| Jagged 1 (↑) |

PD-L1

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctgctgcccg acaaccac                                                 18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
accatgtgat cgcgcttctc                                               20
```

METHOD OF TREATING AUTOIMMUNE DISEASE WITH MESENCHYMAL STEM CELLS

This application is a continuation of U.S. patent application Ser. No. 12/188,922, filed Aug. 8, 2008, now abandoned which claims the benefit of priority of U.S. Provisional Patent Application No. 60/954,973, filed Aug. 9, 2007, the entire contents of each of which are incorporated herein by reference.

Diabetes is characterized by chronic hyperglycemia resulting from a lack of insulin action, along with various characteristic metabolic abnormalities. Diabetes can be broadly divided into type I and type II. Type I diabetes (T1D) is characterized by the loss of pancreatic β-cells of the Langerhans' islets, while type II diabetes is characterized by reductions in both insulin secretion and insulin sensitivity (insulin resistance). In the United States, the prevalence of diabetes is about 2 to 4 percent of the population, with type I (insulin-dependent or IDDM) making up about 7 to 10 percent of all cases.

Type I diabetes mellitus is characterized by the dysfunction of the pancreas to produce insufficient or no insulin. This disorder is caused by autoimmune-mediated destruction of the pancreatic 3-cells. Autoimmunity associated with type I diabetes mellitus involves the participation of both B and T autoreactive lymphocytes. Indeed, up to 98% of type I diabetes mellitus patients have antibodies against one or more of their own β-cell antigens. These include: insulin (Atkinson, et al., *Diabetes* 35:894-98 (1986)); the major of the 2 isoforms of glutamic acid decarboxylase (GAD) 65 (Atkinson, et al., *J. Clin. Invest.* 91:350-56 (1993)); two of the protein tyrosine phosphatases, insulinoma antigen-2 and insulinoma antigen-2b (IA-2 and IA-2β) (Lu, et al., *Proc. Natl. Acad. Sci. USA* 93:2307-11 (1996); Lan, et al., *Proc. Natl. Acad. Sci. USA* 93:6367-70 (1996)); and the heterogeneous islet cell cytoplasmic antigens (ICAs) (Gorus, et al., *Diabetologia* 40:95-99 (1997); Strebelow, et al., *Diabetologia* 42:661-70 (1999)). A minority of type I diabetes mellitus patients also have serum antibodies to a glycosylated islet cell membrane antigen, GLIMA (Aanstoot, et al., *J. Clin. Invest.* 97:2772-83 (1996)). More recently, autoantibodies to other new antigens of protein tyrosine phosphatases, IA-2/ICA512 and IA-2β/phogrin, expressed by pancreatic islet cells, have also been detected in type I diabetes mellitus patients (Kawasaki, et al., *Diabetes* 47:733-42 (1998)).

The generation of autoantibodies to islet cells can be observed for as many as 10 years prior to the onset of clinical diabetes (Luhder, et al., *Autoimmunity* 19:71-78 (1994)). Despite this observation, the existence of autoantibodies is not solely sufficient to cause development of type I diabetes mellitus. This conclusion is based on the finding that infants born of antibody positive type I diabetes mellitus mothers can remain free of disease despite the existence of serum autoantibodies to insulin, GAD and other islet cell antigens. On the other hand, persons with severe genetic B cell deficiency can still develop type I diabetes mellitus (Martin, et al., *N. Engl. J. Med.* 345:1036-40 (2001)). Generally, the level of autoantibodies correlates with the state of β-cell destruction (Irvine, et al., *Diabetes* 26:138-47 (1997); Riley, et al., *N. Engl. J. Med.* 323:1167-72 (1990)). As such, autoantibodies can serve as indicators of the development of autoimmune diabetes. A low level of GAD-specific autoantibodies is associated with a slow breakdown of β-cell function, while a high level of autoantibodies to IA-2 together with the maturation of autoantibody responses elicited against ICAs or GAD are signs for more severe and imminent β-cell failure (Borg, et al., *N. Engl. J. Med.* 86:3032-38 (2001)).

The development of type I diabetes mellitus may be mediated by autoreactive T cells. The most direct indication of this is the direct examination of biopsy tissues obtained near the time of type I diabetes mellitus diagnosis, which show that the islets are infiltrated with activated T cells, primarily of the CD8+ population but also, to a lesser extent, CD4+ cells and macrophages as well (Bottazzo, et al., *N. Engl. J. Med.* 313: 353-60 (1985); Hanninen, et al., *J. Clin. Invest.* 90:1901-10 (1992); Itoh, et al., *J. Clin. Invest.* 92:2313-22 (1993); Imagawa, et al., *Diabetes* 50:1269-73 (2001)). The association of type I diabetes mellitus with the major histocompatibility complex (MHC)-associated susceptibility gene locus, type I diabetes mellitus, has also been well reported (Froguel, *Horm. Res.* 48:55-57 (1997)). Recurrence of organ-specific autoimmunity is responsible for β-cell destruction in diabetics transplanted with a pancreatic graft donated by their discordant, non-diabetic monozygotic twins (Sutherland, et al., *Trans. Assoc. Am. Physic.* 97:80-87 (1984)). Furthermore, type I diabetes mellitus is transferable to non-diabetics given bone marrow transplant donated by diabetic HLA-identical siblings, or allogeneic donors (Marmont, et al., *J. Rheumatol.* 48:13-18 (1997)).

Autoreactive CD4+ cells of the Th1 subset are potentially capable of directly and indirectly causing islet damage; directly via the release of cytotoxic mediators such as nitric oxide or oxygen radicals (Held, et al., *Proc. Natl. Acad. Sci. USA* 87:2239-43 (1990)), and indirectly through the secretion of IL-2 and IFN-γ by activating autoreactive CD8+ T cells and macrophages leading to their infiltration of the islets (Jean-Michel and Burger, *Arthritis. Res.* 1:17-20 (1999)). In this regard, characterization and quantitation of autoreactive T cells in humans are important for the development of an improved diagnosis of type I diabetes mellitus, and intervention strategies for arresting disease progression. However, direct detection of autoreactive T cells in type I diabetes mellitus is more difficult than the detection of autoantibodies. The reason is that CD4+ and CD8+ autoreactive T cells generated in the course of type I diabetes mellitus development are only present at very low frequencies in the circulation of subjects with recent disease onset (Tisch and McDevitt, *Cell* 85:291-97 (1996); Notkins and Lernmar, *J. Clin. Invest.* 108: 1247-52 (2001)).

Assays dependent on in vitro expansion to allow the detection of autoreactive CD4+ T cells in the pool of peripheral blood leucocytes (PBL) of diabetics have been used in some studies. When employing in vitro proliferation assays, PBL of individuals with recent onset of type I diabetes mellitus respond to human insulin (Keller, *Autoimmunity* 3:321-27 (1994)), a spectrum of islet cell antigens (Roep, et al., *Diabetes* 44:278-83 (1995); Brooks-Worrell, et al., *J. Immunol.* 157:5668-74 (1996); Mayer, et al., *J. Clin. Endocrinol. Metab.* 84:2419-24 (1999)), and GAD (Atkinson, *Lancet* 339:458-59 (1992)). Regarding detection, GAD-specific autoreactive T cells can be generated and cloned from peripheral T cells of recent onset type I diabetes mellitus patients who are carrying the disease-susceptible HLA-DR alleles (Endl, et al., *J. Clin. Invest.* 99:2405-15 (1997)). Furthermore, endogenous GAD fragments presented by type I diabetes mellitus-associated HLA class II molecules can be isolated (Nepom, et al., *Proc. Natl. Acad. Sci. USA* 98:1763-68 (2001)).

Autoreactive CD8+ T cells have been detected against two β-cell antigens in diabetic humans, namely GAD 65 and preproIAPP (precursor human islet amyloid polypeptide protein), which are co-secreted with insulin in subjects recently diagnosed with type I diabetes mellitus. GAD 65-specific cytotoxic T cells (CTLs) carrying the disease-associated allele, HLA-A2, following in vitro expansion with a HLA-A2 binding peptide, have been generated from PBL of these individuals (Panina-Bordignon, et al., *J. Exp. Med.* 181:1923-27 (1995)). A recent study describes the presence of an autoreactive CD8+ subset in the circulation of recently diagnosed patients that recognizes a 9 amino acid long immunodominant epitope of preproIAPP in the context of HLA-A2 using an IFN-γ-based ELISPOT assay (Panagiotopoulos, et al., *Diabetes* 52:2647-51 (2003)). The direct detection and quantitation of circulating autoreactive T cells at early disease onset may provide a valuable tool for improved diagnosis of type I diabetes mellitus.

The discovery that diabetics mount humoral and cellular immune responses against islet cell antigens (ICAs) has led to the testing of ICAs and their analogs as candidates for therapeutic agents for better treatment of type I diabetes mellitus at its prediabetic and diabetic stages. In addition, various immunological intervention strategies aimed at direct targeting of the autoreactive T cells have also been investigated. Nevertheless, new and alternative methods for treating and/or preventing the onset of type I diabetes mellitus are needed.

Thus, the invention provides methods of treating or preventing the onset of type 1 diabetes (T1D) in a subject by administering autologous or allogeneic mesenchymal stem cells to the subject before the complete autoimmune-induced depletion of insulin-producing pancreatic beta cells. The invention is based, in part, upon the observation that mesenchymal stem cells, when administered to a mammalian subject prior to the complete auto-immune induced depletion of insulin-producing pancreatic beta cells, can treat, or even prevent the development of, new onset of type 1 diabetes (T1D).

In one aspect, the invention provides a method of treating new onset type 1 diabetes (T1D) in a subject by administering autologous or allogeneic mesenchymal stem cells to the subject prior to autoimmune-induced complete depletion of insulin-producing pancreatic beta cells. In another aspect, the method of treating new onset type 1 diabetes (T1D) involves administering autologous or allogeneic mesenchymal stem cells to the subject within six months of new onset type 1 diabetes (T1D) diagnosis. In still another aspect, the invention provides a method of treating or preventing new onset type 1 diabetes (T1D) in a human subject determined to be at high risk for the disease by preemptively administering autologous or allogeneic mesenchymal stem cells to the subject.

In certain embodiments, the invention provides methods of treating T1D by administering the mesenchymal stem cells within 10 days of T1D diagnosis. In other embodiments, the mesenchymal stem cells are administered within 24 hours of T1D diagnosis. In still other embodiments, the mesenchymal stem cells are administered at the time of, or even before T1D diagnosis (e.g., following a determination that the subject is at high risk for developing T1D such as by the presence of a predisposing genotype or the initial presence of diabetic autoantibodies or other pre-diabetic autoimmune indicators).

In some embodiments, the method of the invention further includes a second administration of autologous or allogeneic mesenchymal stem cells within ten days of the first administration of autologous or allogeneic mesenchymal stem cells. In further embodiments, the second administration of autologous or allogeneic mesenchymal stem cells is made within one month of the first administration of autologous or allogeneic mesenchymal stem cells. In still further embodiments, the second administration of autologous or allogeneic mesenchymal stem cells may be made within three months, six months, one year, two years, or even five years of the first administration of autologous or allogeneic mesenchymal stem cells.

In certain embodiments, the invention provides methods wherein the mesenchymal stem cells are derived from bone marrow or peripheral blood. In particular embodiments, the bone marrow derived cells comprise CD271-positive mesenchymal stem cells. In further embodiments, the mesenchymal stem cells may be derived from umbilical cord blood cells. In other embodiments, the mesenchymal stem cells may be derived from a population of muscle cells, fat cells, embryonic yolk sac cells, placenta cells, fetal blood cells, fetal skin cells, or adult skin cells.

In general, the invention provides methods of treating or preventing new onset type 1 diabetes (T1D) by administering mesenchymal stem cells to a subject in the early stages of autoimmune-induced loss of pancreatic islet β-cells. The early stages of autoimmune-induced loss of pancreatic islet β-cells may be defined by one or more temporal parameters. In certain embodiments, the mesenchymal stem cells are administered to a subject having an abnormally low, but measurable, serum C-peptide level. Serum C-peptide levels decline with the onset of T1D, and a low, but measurable, level of C-peptide is one indication that the subject is in the early stages of autoimmune-induced loss of pancreatic islet 8-cells. Other temporal indicators of the early stages of autoimmune-induced T1D may further be used to refine the method of the invention.

In particular embodiments, the therapeutic mesenchymal stem cells are administered to a subject having both an abnormally low, but measurable, serum C-peptide level, and an abnormally high blood glucose level in the absence of exogenous insulin administration. In certain embodiments, the abnormally high blood glucose level is a fasting blood glucose level of greater than about 120 mg/dl in the absence of exogenous insulin administration. In further embodiments, the subject has a fasting C-peptide level of about 0.033 nmol/L or greater. In particular embodiments, the subject has a fasting C-peptide level of 0.1 nmol/L or greater. In still further embodiments, the subject has a fasting C-peptide level of 1.0 nmol/L or less. In particular embodiments, the subject has a fasting C-peptide level of about 0.033 nmol/L to about 1.0 nmol/L. In other embodiments, the subject has a fasting C-peptide level of about 0.1 nmol/L to about 1.0 nmol/L. In still further embodiments, the subject manifests a measurable increase in post-oral glucose tolerance test integrated C-peptide level, or, preferably, the subject manifests a measurable increase in stimulated C-peptide test integrated C-peptide level. In particular embodiments, the subject has a measurable increase of 0.54 nmol/L, or less, in post-oral glucose tolerance test integrated C-peptide levels, or, more preferably, the subject manifests an increase of 0.54 nmol/L, or less, in stimulated C-peptide test integrated C-peptide levels.

Other parameter(s) may also be used to indicate the subject's amenability to the method of the invention. For example, in certain embodiments the subject has a detectable level of pancreatic autoantibody. In certain embodiments, the pancreatic autoantibody may be GADAb, ICA, IA-2Ab, or IAA. In further embodiments, the subject has an HbA1c level of 7% or higher.

In still other embodiments of the invention, the mesenchymal stem cells administered to the subject may be autologous mesenchymal stem cells (i.e., derived from the same subject to which they are administered). In particular embodiments, the autologous mesenchymal stem cells are derived from umbilical cord blood.

In further embodiments, the mesenchymal stem cells administered to the subject may be allogeneic mesenchymal stem cells (i.e., derived from individuals of the same species as the subject to which they are administered).

In still further embodiments, the mesenchymal stem cells administered to the subject are CD105 positive. In particular embodiments, the CD105 positive mesenchymal stem cells are plastic-adherent and spindle-shaped cells. In certain embodiments, the CD105 positive mesenchymal stem cells are capable of dividing to form a population of CD105 positive mesenchymal stem cells. In some embodiments, the CD105 positive mesenchymal stem cells are capable of differentiating into a differentiated cell type. In particular embodiments, the CD105 positive mesenchymal stem cells are capable of differentiating into multiple different differentiated cell types. In certain embodiments, the mesenchymal stem cells are capable of differentiating into osteoblasts, chondrocytes, myocytes, adipocytes, and/or neuronal cells. In some embodiments, the CD105 positive mesenchymal stem cells are capable of differentiating into a particular tissue type. In certain embodiments, the mesenchymal stem cells are capable of differentiating into bone, cartilage, muscle, marrow stroma, tendon and/or connective tissue.

In yet other embodiments, the mesenchymal stem cells are positive for one or more mesenchymal stem cell markers such as CD105 (endoglin, SH2), and/or CD73 (ecto-5' nucleotidase, SH3, SH4). In particular embodiments, the mesenchymal stem cells are negative for the markers CD45, CD34, and/or CD14.

In certain embodiments, the mesenchymal stem cells are positive for the markers CD105, CD73 and CD90. In particular embodiments, the mesenchymal stem cells are negative for the markers CD45, CD34, and CD14. In some such embodiments, the mesenchymal stem cells are plastic-adherent when maintained in standard culture conditions and are capable of differentiating in vitro into osteoblasts, adipocytes and/or chondroblasts.

In other useful aspects, the invention provides methods in which, in addition to the autologous or allogeneic mesenchymal stem cells, the subject is further administered an immunosuppressive agent. In particular embodiments, the immunosuppressive agent is prednisone, azathioprine, cyclosporine, antibodies against CD3, antibodies against CD20, or antithymocyte globulin. In certain embodiments, the immunosuppressive agent is administered contemporaneously with the autologous or allogeneic mesenchymal stem cells. In other embodiments, the immunosuppressive agent is administered within one month of the autologous or allogeneic mesenchymal stem cells.

In still other useful aspects, the invention provides methods in which, in addition to the autologous or allogeneic mesenchymal stem cells, the subject is further administered a peptide vaccine. In particular embodiments, the vaccine induces tolerance of insulin-producing cells. In certain embodiments, the vaccine includes an autoimmune type 1 diabetes (T1D) autoantigen. In particular embodiments, the autoantigen is insulin, proinsulin, glutamic acid decarboxylase (GAD65), HSP60, or IA-2 protein tyrosine phosphatase.

In further useful aspects, the invention provides methods in which, in addition to the autologous or allogeneic mesenchymal stem cells, the subject is further administered a non-mitogenic anti-CD3 active compound, such as a CD3 antibody, or a CD3-binding antibody fragment. In particular embodiments, the non-mitogenic anti-CD3 active compound is administered in an injectable form having 5 to 20 mg of the non-mitogenic anti-CD3 active compound.

In another aspect, the invention provides a mesenchymal stem cell expressing an exogenous PD-L1 and/or PD-L2 gene or activity (e.g., a mammalian PD-L1 and/or PD-L2 expression vector, such as an adenovirus vector express PD-L1). In particular embodiments, the mesenchymal stem cell expresses an exogenous PD-L1 gene or activity. In other embodiments, the mesenchymal stem cell overexpresses, relative to a native mesenchymal stem cell, an endogenous PD-L1 and/or PD-L2 gene or activity (e.g., by insertion of a strong transcriptional promoter upstream of the PD-L1 and/or PD-L2 gene, or by selection of epigenetic variants over-expressing one or more of these genes). In particular embodiments, the mesenchymal stem cells overexpressing an endogenous PD-L1 and/or PD-L2 are screened or selected from a group of native mesenchymal stem cells based upon high PD-L1 and/or PD-L2 expression.

In still another aspect, the invention provides a method of treating an autoimmune disease or disorder in a mammal by administering autologous or allogeneic mesenchymal stem cells expressing an exogenous PD-L1 and/or PD-L2 gene or activity, or overexpressing, relative to a native mesenchymal stem cell, an endogenous PD-L1 and/or PD-L2 gene or activity. In particular embodiments, the autoimmune disease or disorder is T1D.

In a further useful aspect, the invention provides a method of treating an autoimmune disease in a mammal by administering autologous or allogeneic mesenchymal stem cells in combination with one or more PD-1-PDL-1/PDL-2 pathway agonists. In certain embodiments the PD-1-PDL-1/PDL-2 pathway agonist is a small molecule, an antibody, and/or a fusion protein. In particular embodiments, the PD-1-PDL-1/PDL-2 pathway agonist is a PD-L1-Fc fusion protein. In certain embodiments, the PD-L1 polypeptide of the PD-L1-Fc fusion protein is a human PD-L1 polypeptide. In particular embodiments, the PD-1-PDL-1/PDL-2 pathway agonist is a fusion protein that includes an anti-PD-1 Fab fragment and an Fc fragment. In further embodiments, the fusion protein includes a linker, e.g., a flexible polypeptide segment joining the PD-L1 polypeptide portion to the Fc polypeptide portion of the PD-L1-Fc fusion protein. In certain embodiments, the autoimmune disease or disorder is T1D.

In another useful aspect, the invention provides a mesenchymal stem cell that underexpresses, relative to a native mesenchymal stem cell, a CXCL10-CXCR3 pathway gene or activity. In one embodiment, the CXCL10-CXCR3-underexpressing mesenchymal stem cell may be one to which a CXCL10 siRNA has been administered (e.g., transfected with). In another embodiment, the mesenchymal stem cell is engineered to express a CXCL10 siRNA (e.g., from an siRNA expression vector construct). In still another embodiment, the CXCL10-CXCR3-underexpressing mesenchymal stem cell may be one that underexpresses one or more endogenous CXCL10-CXCR3 genes or activities (e.g., by insertion of a transcriptional silencer upstream of one or more CXCL10-CXCR3 pathway genes or activities, or by selection of epigenetic variants underexpressing one or more of these genes). In particular embodiments, the mesenchymal stem cells underexpressing an endogenous PD-L1 and/or PD-L2 are screened or selected from a group of native mesenchymal stem cells based upon low CXCL10-CXCR3 pathway expression or activity. In still other embodiments, the CXCL10-CXCR3-underexpressing mesenchymal stem cell may be one which is treated with a CXCL10-CXCR3 pathway antagonist. In particular embodiments, the CXCL10-CXCR3 pathway antagonist is a CXCR3 siRNA and/or a CXCL10 antibody.

In yet another aspect, the invention provides a method of treating an autoimmune disease in a mammal by administering autologous or allogeneic mesenchymal stem cells underexpressing, relative to native mesenchymal stem cells, a CXCL10-CXCR3 pathway gene or activity. In certain embodiments, the autoimmune disease or disorder is T1D. In further embodiments, the method provides for treating an autoimmune disease in a mammal by administering autologous or allogeneic mesenchymal stem cells in combination with one or more antagonists of a CXCL10-CXCR3 pathway gene or activity. In an exemplary embodiment, the CXCL10-CXCR3 pathway antagonist is a small molecule, an antibody, and/or a fusion protein.

Figure 1:
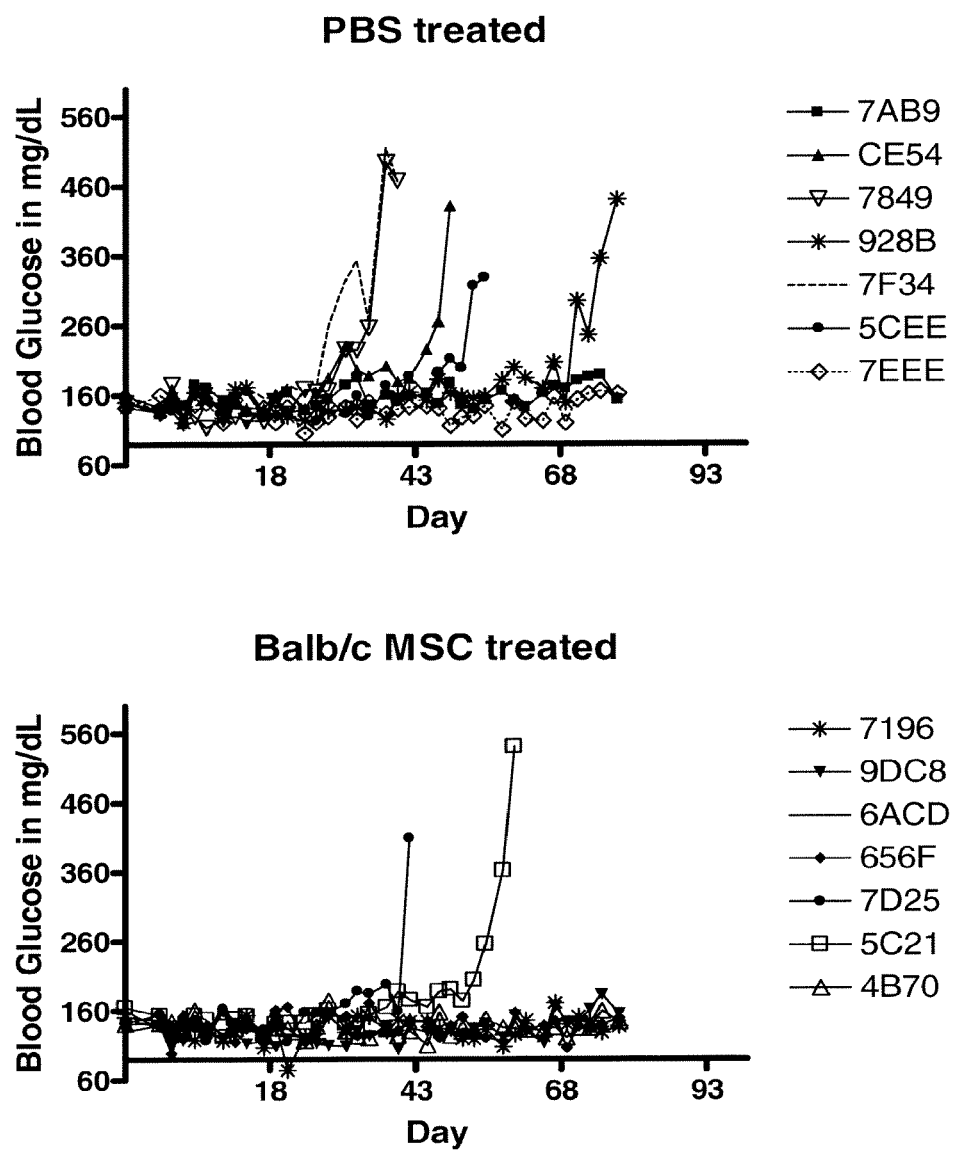
FIG. 1 is a graphical representation of experiments demonstrating that administration of normal mesenchymal stem cells (MSCs) to prediabetic nonobese diabetic (NOD) mice prevents or delays the onset of type I diabetes (T1D).

In general, the invention provides methods and compositions for treating autoimmune disease, such as new onset T1D, with mesenchymal stem cells (MSCs). In particular, the invention provides compositions and beneficial methods of delivery of MSCs to patients with early onset diabetes. The invention further provides genes and markers identified by expression profile analysis of MSCs, including Programmed death 1 (PD-1)—Programmed death ligand 1 (PD-L1) and Programmed death ligand 2 (PD-L2) as well as the components of the CXCL10-CXCR3 pathway, which provide new therapeutic targets that may be used in the treatment of patients with type I diabetes.

DEFINITIONS

The singular forms "a," "an," and "the" include plural reference unless the context clearly dictates otherwise.

All numbers expressing quantities of ingredients, reaction conditions, and so forth used in the specification and claims are to be understood as being modified in all instances by the term "about," wherein about signifies, e.g., ±5%, ±10%, ±15%, ±20%, or ±25%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The term "agonist" as used herein, is meant to refer to an agent that mimics or up-regulates (e.g., potentiates or supplements) the bioactivity of a protein. An agonist can be a wild-type protein or derivative thereof having at least one bioactivity of the wild-type protein. An agonist can also be a compound that up-regulates expression of a gene or increases at least one bioactivity of a protein. An agonist can also be a compound that increases the interaction of a polypeptide with another molecule, e.g., a target peptide or nucleic acid.

"Antagonist" as used herein is meant to refer to an agent that down-regulates (e.g., suppresses or inhibits) at least one bioactivity of a protein. An antagonist can be a compound that inhibits or decreases the interaction between a protein and another molecule, e.g., a target peptide or enzyme substrate. An antagonist can also be a compound that down-regulates expression of a gene or which reduces the amount of expressed protein present.

The term "antibody" as used herein refers to both polyclonal and monoclonal antibody. The term encompasses not only intact immunoglobulin molecules, but also such fragments and derivatives of immunoglobulin molecules (such as single chain Fv constructs, diabodies, and fusion constructs) that retain a desired antibody binding specificity, as may be prepared by techniques known in the art.

The terms "array" or "matrix" is means an arrangement of addressable locations or "addresses" on a device. The locations can be arranged in two-dimensional arrays, three-dimensional arrays, or other matrix formats. The number of locations can range from several to at least hundreds of thousands. Most importantly, each location represents a totally independent reaction site. A "nucleic acid array" refers to an array containing nucleic acid probes, such as oligonucleotides or larger portions of genes. The nucleic acid on the array is preferably single stranded. Arrays wherein the probes are oligonucleotides are referred to as "oligonucleotide arrays" or "oligonucleotide chips." A "microarray," also referred to herein as a "biochip" or "biological chip," is an array of regions having a density of discrete regions of at least about 100/cm$^2$, and preferably at least about 1000/cm$^2$. The regions in a microarray have typical dimensions, e.g., diameters, in the range of between about 10-250 um, and are separated from other regions in the array by about the same distance.

As used herein, the term "autoimmune disease" means a disease resulting from an immune response against a self tissue or tissue component, including both self antibody responses and cell-mediated responses. The term autoimmune disease, as used herein, encompasses organ-specific autoimmune diseases, in which an autoimmune response is directed against a single tissue, such as type I diabetes mellitus (T1D), Crohn's disease, ulcerative colitis, myasthenia gravis, vitiligo, Graves' disease, Hashimoto's disease, Addison's disease and autoimmune gastritis and autoimmune hepatitis. The term autoimmune disease also encompasses non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include pernicious anemia including some of autoimmune gastritis, primary biliary cirrhosis, autoimmune thrombocytopenia, Sjogren's syndrome, multiple sclerosis and psoriasis. One skilled in the art understands that the methods of the invention can be applied to these or other autoimmune diseases, as desired.

The term "biological sample" as used herein, refers to a sample obtained from a subject, e.g., a human or from components (e.g., tissues) of a subject. The sample may be of any biological tissue or fluid. Frequently the sample will be a "clinical sample" which is a sample derived from a patient. Such samples include, but are not limited to bodily fluids which may or may not contain cells, e.g., blood, synovial fluid; tissue or fine needle biopsy samples, such as from bone, cartilage or tissues containing mesenchymal cells. Biological samples may also include sections of tissues such as frozen sections taken for histological purposes.

The term "biomarker" of a disease related to bone or cartilage formation or resorption refers to a gene that is up- or down-regulated in a diseased cell of a subject having such a disease, relative to a counterpart normal cell, which gene is sufficiently specific to the diseased cell that it can be used, optionally with other genes, to identify or detect the disease. Generally, a biomarker is a gene that is characteristic of the disease.

The terms "cell culture" and "culture" encompass the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture," or "organotypic culture" may occasionally be used interchangeably with the term "cell culture."

The term "derivative" refers to the chemical modification of a compound, e.g., a polypeptide, or a polynucleotide. Chemical modifications of a polynucleotide can include, for example, replacement of hydrogen by an alkyl, acyl, or amino group. A derivative polynucleotide encodes a polypeptide which retains at least one biological or immunological function of the natural molecule. A derivative polypeptide can be one modified by glycosylation, pegylation, or any similar process that retains at least one biological or immunological function of the polypeptide from which it was derived.

The term "expression profile," which is used interchangeably herein with "gene expression profile," "finger print" and "expression pattern", refers to a set of values representing the activity of about 10 or more genes. An expression profile preferably comprises values representing expression levels of at least about 20 genes, preferably at least about 30, 50, 100, 200 or more genes.

"Genes that are up- or down-regulated" in a particular process, e.g., in a mesenchymal stem cell, refer to genes which are up- or down-regulated by, e.g., a factor of at least about 1.1 fold, 1.25 fold, 1.5 fold, 2 fold, 5 fold, 10 fold or more. Exemplary genes that are up- or down-regulated during bone and cartilage formation are set forth in Tables 1, 2, 5, 6 and/or 7. "Genes that are up- or down-regulated in a disease" refer to the genes which are up- or down-regulated by, e.g., at least about 1.1 fold, 1.25 fold, 1.5 fold, 2 fold, 5 fold, 10 fold or more in at least about 50%, preferably 60%, 70%, 80%, or 90% of the patients having the disease.

The term "isolated," used in reference to a single cell or clonal cell cluster, e.g., a mesenchymal stem cell or clonal colony thereof, means that the cell is substantially free of other nonclonal cells or cell types or other cellular material with which it naturally occurs in the tissue of origin (e.g., bone or adipose tissue). A sample of mesenchymal stem cells is "substantially pure" when it is at least 60%, or at least 75%, or at least 90%, and, in certain cases, at least 99% free of cells other than cells of clonal origin. Purity can be measured by any appropriate method, for example, by fluorescence-activated cell sorting (FACS).

As used herein, the terms "label" and "detectable label" refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens), and the like. The term "fluoresce" refers to a substance or a portion thereof, which is capable of exhibiting fluorescence in the detectable range. Particular examples of labels which may be used under the invention include fluorescein, rhodamine, dansyl, umbelliferone, Texas red, lumina, NADPH, alpha-beta-galactosidase, and horseradish peroxidase.

A "precursor cell", or "progenitor cell", refers to a cell that has the capacity to create progeny that are more differentiated than itself. For example, the term may refer to an undifferentiated cell or a cell differentiated to an extent short of final differentiation that is capable of proliferation and giving rise to more progenitor cells having the ability to generate a large number of mother cells that can in turn give rise to differentiated or differentiable daughter cells. In certain embodiments, the term progenitor cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. By this definition, stem cells may also be progenitor cells, as well as the more immediate precursors to terminally differentiated cells. Exemplary precursor cells include osteoprogenitor cells such as for example, mesenchymal precursor cells, osteoblasts, and chondroblasts.

As used herein, a nucleic acid or other molecule attached to an array is referred to as a "probe" or "capture probe." When an array contains several probes corresponding to one gene, these probes are referred to as "gene-probe set." A gene-probe set can consist of, e.g., 2 to 10 probes, preferably from 2 to 5 probes and most preferably about 5 probes.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate a bioactivity.

A "subject" can be a mammal, e.g., a human, primate, ovine, bovine, porcine, equine, feline, canine and a rodent (rat or mouse).

The term "treating" a disease in a subject or "treating" a subject having a disease refers to providing the subject with a pharmaceutical treatment, e.g., the administration of a drug, such that at least one symptom of the disease is decreased.

Treating a disease can be preventing the disease, improving the disease or curing the disease.

A "variant" of a polypeptide refers to a polypeptide having the amino acid sequence of the polypeptide, in which one or more amino acid residues are altered. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR). The term "variant," when used in the context of a polynucleotide sequence, encompasses a polynucleotide sequence related to that of a gene of interest or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

Mesenchymal Stem Cells

The invention provides mesenchymal stem cell (MSC) compositions and methods for the treatment of autoimmune disease, such as T1D. MSCs are multipotent cells that have the potential to give rise to cells of various mesenchymal and non-mesenchymal lineages, including adipose, bone, and cartilage (Pittenger, et al., *Science* 284:143-7 (1999)). MSCs are a component of bone marrow stroma and although bone marrow provides a facile source of MSCs, MSCs can be isolated from most adult and fetal tissues, including fat and muscle tissue, umbilical cord blood, and fetal blood using methods known in the art (see, e.g., daSilvaMeirelles, et al., *J. Cell Sci.* 119:2204-13 (2006); Erices, et al., *Br. J. Haematol.* 109:235-42 (2000); Campagnoli, et al., *Blood* 98:2396-402 (2001)). In the bone marrow, MSCs are essential because they provide the supportive microenvironment for growth, differentiation, and function of hematopoietic stem cells (HSCs), which give rise to all components of the immune and blood systems (Dazzi, et al., *Blood Rev.* 20:161-71 (2006)). Because MSCs and other multi-potent progenitor cells have been shown to give rise to multiple cell types, use of MSCs as an alternative source of cells for cellular replacement therapies is being investigated.

MSCs are the formative pluripotential blast cells found inter alia: in bone marrow, blood, dermis and periosteum that are capable of differentiating into more than one specific type of mesenchymal or connective tissue (i.e. the tissues of the body that support the specialized elements; e.g., adipose, osseous, stroma, cartilaginous, elastic and fibrous connective tissues) depending upon various influences from bioactive factors, such as cytokines.

Approximately 30% of human marrow aspirate cells adhering to plastic are considered as MSCs. These cells can be expanded in vitro and then induced to differentiate. The fact that adult MSCs can be expanded in vitro and stimulated to form bone, cartilage, tendon, muscle or fat cells render them attractive for tissue engineering and gene therapy strategies. In vivo assays have been developed to assay MSC function. MSCs injected into the circulation can integrate into a number of tissues described hereinabove. Specifically, skeletal and cardiac muscle can be induced by exposure to 5-azacytidine and neuronal differentiation of rat and human MSCs in culture can be induced by exposure to β-mercaptoethanol, DMSO or butylated hydroxyanisole (Woodbury, *J. Neurosci. Res.* 61:364-370 (2000)). Furthermore, MSC-derived cells are seen to integrate deep into the brain after peripheral injection as well as after direct injection of human MSCs into rat brain; they migrate along pathways used during migration of neural stem cells developmentally, become distributed widely and start to lose markers of HSC specialization (Azizi, *Proc. Natl. Acad. Sci. USA* 95:3908-3913)1998)). Methods for promoting mesenchymal stem and lineage-specific cell proliferation are disclosed in U.S. Pat. No. 6,248,587.

Epitopes on the surface of the human mesenchymal stem cells (hMSCs) such as SH2, SH3 and SH4 described in U.S. Pat. No. 5,486,359 can be used as reagents to screen and capture mesenchymal stem cell population from a heterogeneous cell population, such as exists, for example, in bone marrow. Precursor mesenchymal stem cells that are positive for CD45 are preferably used according to this aspect of the present invention, since these precursor mesenchymal stem cells can differentiate into the various mesenchymal lineages.

Many different methods have been developed to isolate and expand MSCs. The criteria for defining multipotent mesenchymal stromal (stem) cells has been established by the Mesenchymal and Tissue Stem Cell Committee of the International Society of Cellular Therapy in its "Position Paper" (Dominici, et al., *Cytotherapy* 8:315-17 (2006)).

First, MSCs must be plastic-adherent when maintained in standard culture conditions. Plastic adherence is a well-described property of MSC, and even unique subsets of MSC that have been described maintain this property (Colter, et al., *Proc. Natl. Acad. Sci. USA* 97:3213-18 (2000); Jiang, et al., *Nature* 418:41-49 (2002)). While MSC may be maintained, and possibly expanded, without adherence (Baksh, et al., *Exo. Hematol.* 31:723-32 (2003)), these protocols typically require very specific culture conditions, and these cells, if maintained under more standard conditions, would be expected to demonstrate adherence if the cells are to be considered a population of MSC.

Second, $\geq 95\%$ of the MSC population must express CD105, CD73 and CD90, as measured, e.g., by flow cytometry. Additionally, most ($\geq 98\%$) of the MSC population must lack expression of CD45, CD34, CD14 or CD11b, CD79α or CD19 and HLA-DR surface molecules. Surface antigen (Ag) expression, which allows for a rapid identification of a cell population, has been used extensively in immunology and hematology. MSCs should express CD105 (known as endoglin and originally recognized by the MAb SH2), CD73 (known as ecto 5' nucleotidase and originally recognized by the mAb SH3 and SH4) and CD90 (also known as Thy-1). To assure that studies of heterogeneous populations of MSCs are not confounded by other contaminating cell types, lack of expression of hematopoietic Ags may be used as additional criteria for identification and purification of MSCs as they are not known to express these Ag. For this purpose, a panel of Ags may be used to exclude the contaminating cells most likely to be found in MSC cultures. CD45 is a pan-leukocyte marker; CD34 marks primitive hematopoietic progenitors and endothelial cells; CD14 and CD11b are prominently expressed on monocytes and macrophages, the most likely hematopoietic cells to be found in an MSC culture; CD79α and CD19 are markers of B cells that may also adhere to MSCs in culture and remain vital through stromal interactions; and HLA-DR molecules are not expressed on MSCs unless stimulated, e.g. by IFN-γ. Only one of the two macrophage and B-cell markers needs to be tested. The investigator may select the marker(s) that is (are) most reliable in their laboratory.

Third, MSCs must be capable of differentiating into osteoblasts, adipocytes and chondroblasts in vitro. The biologic property that most uniquely identifies MSCs is their capacity for trilineage mesenchymal differentiation. Thus, cells may be shown to differentiate to osteoblasts, adipocytes and chondroblasts using standard in vitro tissue culture-differentiating conditions. Differentiation to osteoblasts can be demonstrated by staining with Alizarin Red or von Kossa staining. Adipocyte differentiation is most readily demonstrated by staining with Oil Red O. Chondroblast differentiation is demonstrated by staining with Alcian blue or immunohistochemical staining for collagen type II. Most published protocols for such differentiations are similar, and kits for such assays are now commercially available. Accordingly, demonstrating differentiation should be feasible for all investigators.

Several of the above-listed criteria merit further comment. First, as many surface markers (both positive and negative) may be tested as deemed important especially as it relates to the particular application. The optimum flow cytometric assay would utilize multicolor analyses (i.e. double staining, triple staining, etc.) to demonstrate that individual cells co-express MSC markers and lack hematopoietic Ag. The proposed panel of Ag does not uniquely identify MSCs compared with some other cell types (Sabatini, et al., *Lab. Invest.* 85:962-71 (2005)), however, the surface phenotype, in conjunction with the other functional criteria, best identifies MSCs with the current state of knowledge.

Second, MSC express HLA-DR surface molecules in the presence of IFN-γ but not in an unstimulated state. Thus, if HLA-DR expression is found, and in fact, such expression may be desirable for some applications, the cells may still be termed MSCs, assuming the other criteria are met, but should be qualified with adjectives, such as "stimulated MSC" or other nomenclature to indicate that the cells are not in the baseline state.

Third, the level of MSC purity ($\geq 95\%$ expression of CD105, CD73, CD90; $\leq 2\%$ expression of hematopoietic Ag) may be considered as a minimal guideline. Greater levels of demonstrated purity may be required for certain applications.

Finally, MSCs have great propensity for ex vivo expansion. Investigators who utilize extensively passaged cells may be well served by verifying a normal karyotype to reduce the probability of chromosomal abnormalities, including potentially transforming events. Such events could potentially lead to the establishment of a novel cell line, and the resulting cells should no longer be considered MSCs. However, karyotype analysis is not being recommended for routine identification of MSCs.

As described further below, the human mesenchymal stem cells can be used as hosts for foreign genes for the expression of gene products in systemic or localized targets. The human mesenchymal stem cells of the invention can be engineered (transduced or transformed or transfected) with genetic material of interest. The engineered human mesenchymal stem cells can be cultured in conventional nutrient media modified as appropriate for activating promoters, selecting transformants or amplifying exogenous genes therein. The culture conditions, such as temperature, pH and the like, can be those previously used with engineered human mesenchymal stem cells. See, for example, Gerson, et al., U.S. Pat. No. 5,591,625. Mesenchymal stem cells can be treated with IFNγ to stimulate MHC presentation by the mesenchymal stem cells.

Unless otherwise stated, genetic manipulations are performed as described in Sambrook and Maniatis, Molecular Cloning: A Laboratory Manual, Cold Spring Harbor Laboratory, 1989.

Treatment Methods and Compositions

In the prophylaxis or treatment of disease states, the recipient may be only required to undergo a single administration after which disease remission is realized on a permanent basis. Alternatively, depending upon observation of follow-up monitoring, any subsequent administration may be of greater or lesser doses. Such procedures and monitoring regimens are well known to those who are versed in the field of immune therapy, infectious disease, oncology, epidemiology and the like.

The dosage of the active ingredient varies within wide limits and will, of course be fitted to the individual requirements in each particular case. In general, in the case of parenteral administration, it is customary to administer from about 0.5 to about 5 million cells per kilogram of recipient body weight. The number of cells used will depend on the weight and condition of the recipient and other variables known to those of skill in the art. The cells can be administered by a route that is suitable for the particular disease state to be treated. In the case of non-specific induction of hyporesponsiveness of the immune response, mesenchymal stem cells can be administered systemically, i.e., parenterally, intravenously or by injection. In the case of induction of genetically engineered or modified MSCs, the antigen-modified mesenchymal stem cells can be targeted to a particular tissue or organ.

The cells can be suspended in an appropriate diluent, at a concentration of from about $5 \times 10^6$ to about $50 \times 10^6$ cells/ml. Suitable excipients for injection solutions are those that are biologically and physiologically compatible with the recipient, such as buffered saline solution. The composition for administration should be sterile, stable, and the like, as is appropriate for administration into an individual.

The methods of the present invention are particularly applicable to therapy of autoimmune disease, particularly T1D, and should preferably inactivate or eliminate the response to autoantigen specifically, without compromising other aspects of the immune system.

Although not limited to the treatment of autoimmune disease, the mesenchymal stem cells and method of the invention can accordingly be appropriately applied to treatment strategies requiring immunosuppressive reagents. Also contemplated is the modification of and expansion of mesenchymal stem cells in vitro for use in cellular immunotherapy, the in vivo administration of the immunosuppressive mesenchymal stem cells for treating or preventing unwanted immune responses. One aspect of the invention is the development of the mesenchymal stem cells into a vehicle for delivering inhibitory signals or antigen to target a specific cellular response, the development of vaccines with the mesenchymal stem cells modified as described herein for either target specific or systemic delivery of immunosuppression for prophylaxis and therapy of disease.

PD-1—PD-L1/PD-L2 Pathway

The methods and compositions of the invention may optionally include PD-1—PD-L1/PD-L2 pathway proteins, nucleic acids and agonists (see Yadav and Sarvetnick, *Rev. Diab. Stud.* 3:6-10 (2006)). Exemplary nucleic acids and polypeptides of this pathway are known in the art and include GenBank polypeptide listings as well as the GenBank nucleic acid listings.

PD-1 (programmed death-1) is a type I transmembrane protein and its extracellular region contains a single immunoglobulin V (IgV) domain. Its cytoplasmic region has two tyrosines, each of which constitute an immunoreceptor tyrosine-based inhibition motif (ITIM) and an immunoreceptor tyrosine-based switch motif (ITSM) (Shlapatska, et al., *J. Immunol.* 166:5480-87 (2001)). It is the ITSM that is required for the inhibitory activity of PD-1. PD-1 exists as a monomer on cell surfaces due to the lack of membrane proximal cysteine (Zhang, et al., *Immunity* 20:337-47 (2004)). Co-localization of PD-1 with TCR/CD28 on T cells is essential for its inhibitory function that involves the CD28-mediated activation of phosphatidylinositol-3-kinase (PI3K) (Greenwald, et al., *Ann. Rev. Immunol.* 23:515-48 (2005)). PD-1 can be induced, not only on CD4 and CD8 T cells, but also on B cells and myeloid cells. NK-T cells have also been shown to express low levels of PD-1. During thymic development, PD-1 is predominantly expressed on CD4-CD8-T cells and also on double negative γδ T cells (Nishimura, et al., *J. Exp. Med.* 191:891-898 (2000)). There is also some evidence in support of the role of PD-1 as a regulator of positive selection (Blank, et al., *J. Immunol.* 171:4574-81 (2003)). PD-1-deficient mice exhibit an overactivation of immune responses and thus support the development of autoimmune diseases (Nishimura, et al., *Int. Immunol.* 10:1563-72 (1998); Nishimura, et al., *Immunity* 11:141-51 (1999); Nishimura, et al., *Science* 291:319-22 (2001)). Also, PD-1 knock-out mice display a more vigorous T cell response as compared to normal controls (Iwai, et al., *J. Exp. Med.* 198:39-50 (2003)). These findings suggest that the engagement of PD-1 on T cells predominantly leads to the generation of negative signals.

PD-1 has two ligands, namely PD-L1 (B7-H1) and PD-L2 (B7-DC), and their similarity with B7 molecules prompted their identification using databased search (Freeman, et al., *J. Exp. Med.* 192:1027-34 (2000); Latchman, et al., *Nat. Immunol.* 2:261-68 (2001); Tseng, et al., *J. Exp. Med.* 193:839-46 (2001)). PD ligands are type I transmembrane proteins with IgV and IgC domains in their extracellular region. PD-L2 has been shown to have an affinity for PD-1 that is two to six times higher than that of PD-L1 (Zhang, et al., *Immunity* 20:337-47 (2004)). These PD ligands show a distinct pattern of expression; PD-L1 is more widely expressed than PD-L2 (Freeman, et al., *J. Exp. Med.* 192:1027-34 (2000); Latchman, et al., *Nat. Immunol.* 2:261-68 (2001); Tseng, et al., *J. Exp. Med.* 193:839-46 (2001); Dong, et al., *Nat. Med.* 5:1365-69 (1999)). PD-L1 is expressed on T and B cells, dendritic cells and macrophages and also becomes upregulated upon activation (Liang, et al., *Eur. J. Immunol.* 33:2706-16 (2003); Yamzaki, et al., *J. Immunol.* 169:5538-45 (2002); Ishida, et al., *Immunol. Lett.* 84:57-62 (2002)). Interestingly, PD-L1 has also been shown to be expressed by non-hematopoietic cells including endothelial cells in the heart, β-cells in the pancreas, and also in non-lymphoid organs namely lung, muscle and placenta (Liang, et al., *Eur. J. Immunol.* 33:2706-16 (2003); Ishida, et al., *Immunol. Lett.* 84:57-62 (2002); Weidl, et al., *Brain* 126:1026-35 (2003); Rodig, et al., *Eur. J. Immunol.* 33:3117-26 (2003); Petroff et al., *Biol. Reprod.* 68:1496-1504 (2003)). The expression of PD-L1 in non-lymphoid tissues suggests a potential regulatory role of PD-L1 in regulating autoreactive T and B cells in target organs. On the other hand, PD-L2 is more restricted and its expression can be observed in dendritic cells and macrophages. There is also evidence that the expression of PD-L1 and PD-L2 can be influenced by Th1 and Th2 cytokines, such as IFN-γ and IL-4, which have been shown to up-regulate PD-L1 and PD-L2, respectively (Loke and Allison, *Proc. Natl. Acad. Sci. USA* 100:5336-41 (2003)).

CXCL10-CXCR3 Pathway

The methods and compositions of the invention may optionally include CXCL10-CXCR3 pathway proteins, nucleic acids and agonists. Exemplary nucleic acids and polypeptides of this pathway are known in the art and include the GenBank polypeptide listings as well as the GenBank nucleic acid listings.

The foregoing detailed description includes many specific details. The inclusion of such detail is for the purpose of illustration only and should be understood not to limit the invention. In addition, features in one embodiment may be combined with features in other embodiments of the invention. The patent and scientific literature referred to in this description establishes knowledge that is available to those of skill in the art. The issued U.S. patents, allowed applications, published foreign applications, and references, including GenBank database sequences, that are cited herein are hereby incorporated by reference to the same extent as if each was specifically and individually indicated to be incorporated by reference. To the extent publications and patents or patent applications incorporated by reference contradict the invention contained in the specification; the specification will supersede any contradictory material.

EXAMPLES

This invention is further illustrated by the following examples, which should not be construed as limiting.

Example 1

MSCs to Treat New Onset Type 1 Diabetes

In these illustrative examples, MSCs were delivered to NOD mice to prevent and reverse diabetes. Systemic delivery of normal Balb/c MSCs derived from Balb/c bone marrow delayed the onset of diabetes and reversed established hyperglycemia if delivered within one week of onset of autoimmune disease. In contrast, the delivery of MSCs derived from pre-diabetic female NOD mice bone marrow did not delay diabetes onset. This data supports the therapeutic benefit of early delivery of MSCs to patients with developing autoimmune, early onset diabetes.

Animals and Injections

Six to eight week old female Balb/c (B/c) and C57BL/6 (B6) mice and 4-6 week old female pre-diabetic NOD/Lt (NOD) mice that had been purchased from the Jackson Laboratory were used to generate MSCs. For in vivo experiments, 10 week old pre-diabetic female NOD mice were injected with 500,000 MSCs i.v. each week for 4 weeks. For reversal studies, mice were given one dose of 500,000 B/c MSCs at the various times up to 90 days after 10 weeks of age. Blood glucose measurements were taken two to three times a week starting the week before MSC administration. Mice with blood glucose values greater than 250 mg/dL for three consecutive readings were considered diabetic.

MSC Generation and Propagation

Multiple independent sets of MSCs were generated for use in these experiments. MSCs were isolated by plastic adherence after culturing pooled bone marrow cells for 7 days. For each MSC generation, bone marrow cells were flushed from both femurs and tibias of 15-40 mice. Cells were flushed with a 27 gauge needle using high glucose DMEM media (Gibco), then pooled and treated with Puregene RBC Lysis Solution (Gentra Systems) to lyse red blood cells. Following RBC lysis, cells were washed with high glucose DMEM, counted and plated in high glucose DMEM media containing 10% FBS (Gibco 10099-158, lot 1229021), 1× penicillin/streptomycin (Gibco) and 2 mM L-glutamine (Gibco). Five days after initial plating, the media was removed and fresh media added back. On day 7 the cells were harvested by treatment with trypsin-EDTA (0.05%; Gibco) for 5 minutes at 37° C. followed by gentle scraping and pooling to form "passage 1" cell pool (p1). These cells were then washed with $Ca^{+2}/Mg^{+2}$ free PBS before trypsin-EDTA addition and the reaction was stopped by adding a 1:1 volume of FBS to trypsin-EDTA.

MSC Tracking

MSCs were generated from GFP transgenic C57BL6 mice purchased from Jackson Laboratories as described above. One million MSCs were delivered i.p. to diabetic and non-diabetic NOD mice and 4 days later organs were harvested, homogenized on trizol (Invitrogen) and snap frozen. RNA was isolated using standard techniques and the expression of GFP was analyzed by quantitative PCR. The relative GFP copy number for each tissue was extrapolated using various amounts of plasmid containing a known number of GFP genes.

MSCs Derived from Normal Mice Delay Diabetes Onset

Normal allogeneic MSCs were systemically administered to pre-diabetic NOD animals to determine whether systemic delivery could alter the course of disease. MSCs were derived from the bone marrow of 6-8 week old Balb/c mice. MSCs were isolated by adherence to plastic in 10% FBS and cultured for several passages. After 2 passages, murine MSCs were positive for CD105 and CD44 and negative for CD34. MSCs were injected into 10 week old (pre-diabetic) female mice once a week for weeks as shown in FIG. 1. Groups of NOD animals treated with Balb/c MSCs were compared to animals treated with PBS vehicle control. Diabetes development was determined by blood glucose monitoring of all animals. Onset of diabetes was determined to be when blood glucose levels were >250 mg/dL. Onset occurred in vehicle control animals starting at 20 days post-treatment (top panel), whereas disease onset in Balb/c treated mice occurred between 43-60 days post-treatment (bottom panel). In detail, FIG. 1 shows that normal allogeneic MSCs prevent the onset of diabetes in NOD mice. Pre-diabetic female NOD mice (10 weeks of age) were injected intravenously once per week for 4 weeks with PBS (top panel) or 500,000 MSCs (bottom panel) derived from bone marrow of Balb/c mice. Each line represents a single NOD mouse. This is a representative Figure depicting data from 3 experiments. For each experiment, a minimum of 7 mice per group was used.

Therefore, allogeneic MSC treatment significantly delayed the onset of diabetes development in this cohort of NOD mice.

MSCs Track to Pancreatic Lymph Nodes and Spleen

The effects of MSCs on the course of diabetes development in NOD animals were further investigated in tracking experiments designed to detect the presence of MSCs in diabetic target organs, such as the spleen and pancreatic draining lymph node (PDLN). In order to track MSCs in vivo, MSCs were generated from the bone marrow of B6 GFP-transgenic mice. GFP-MSCs were injected into pre-diabetic and diabetic NOD mice and tissues were harvested and quantitated by PCR for GFP expression 4 days post injection.

Figure 2:
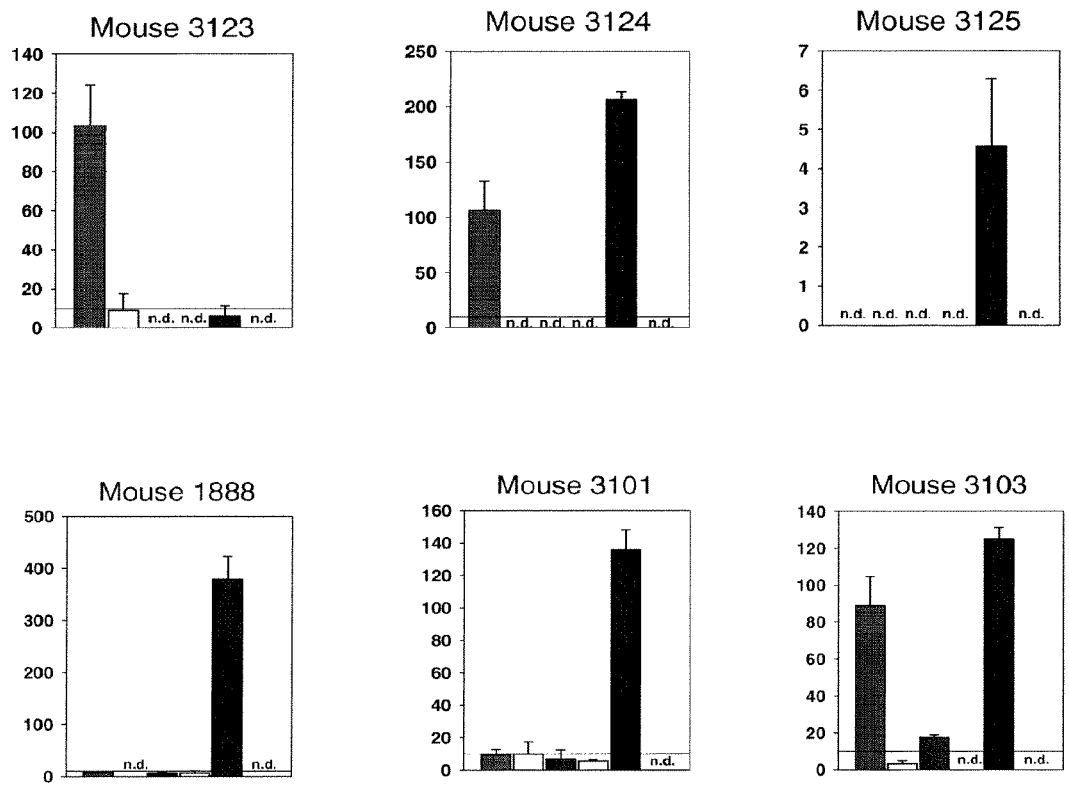
FIG. 2 is a graphical representation of experiments demonstrating that green fluorescent protein (GFP) transgenic MSCs track to pancreatic lymph nodes and spleen when administered to pre-diabetic (top panels) and diabetic (bottom panels) NOD mice. Tissues examined (bars from left to right) are spleen, liver, kidney, mesenteric lymph nodes, pancreatic lymph nodes, and non-draining peripheral lymph nodes.

FIG. 2 shows that transgenic MSCs preferentially tracked to the PDLN and the spleen in both pre-diabetic (top panels) and diabetic (bottom panels) animals. FIG. 2 depicts relative GFP copy number in organs harvested from pre-diabetic (mice 3123, 3124, 3125) and diabetic (mice 1888, 3101, 3103) female NOD mice that had been administered a one time dose of MSCs generated from the bone marrow of GFP transgenic C57BL/6 mice. 1×10$^6$ GFP C57BL/6 MSCs were injected i.p., and four days later, organs were harvested and processed for RNA. The relative GFP copy number detected in each organ was determined by quantitative PCR and plotted. Each panel represents data from an individual mouse. Each bar, left to right, represents a specific organ as indicated: first bar (dark grey) is spleen, second bar (light grey) is liver, third bar (darkest grey) is kidney, fourth bar (white) is mesenteric lymph node, fifth bar (black) is pancreatic lymph node, sixth bar is a pool of inguinal/brachial/axillary lymph nodes (n.d. indicates "not detected").

These results show that MSCs are able to traffic to the PDLN and the spleen where autoreactive T cells interact with auto antigens before homing to the beta cells in the islets in the pancreas. Accordingly, MSCs have an intrinsic ability to home to areas of inflammation presently in disease and exert their immunosuppressive functions on T cells that are present in target organs.

Normal, but not NOD, Allogeneic MSCs Delay Diabetes Onset

The therapeutic potential of MSCs in the treatment of diabetes was further investigated by treating pre-diabetic NOD mice with both normal allogeneic Balb/c MSCs and NOD MSCs (derived from 10-week old, pre-diabetic NOD mice) once a week for 4 weeks and monitoring disease development by blood glucose monitoring. The diabetic disease status of each animal was monitored beginning 1 week after the first injection of MSCs. Mice were non-diabetic until the first occurrence of high blood glucose, at which point they were deemed diabetic.

Figure 3:
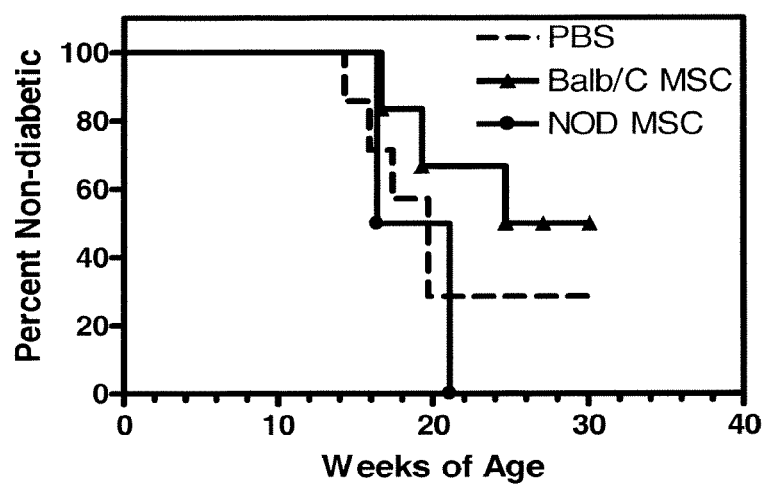
FIG. 3 is a graphical representation of experiments demonstrating that administration of normal allogeneic MSCs, but not NOD MSCs, delays the onset of diabetes in prediabetic NOD mice.

The results demonstrated that normal allogeneic MSCs significantly delay onset of diabetes. FIG. 3 shows that the administration of normal allogeneic MSCs (Balb/C MSC, triangles) delays the onset of diabetes, while the administration of NOD MSCs (NOD MSC, circles) does not. Pre-diabetic female NOD mice (10 weeks of age) were injected intravenously once per week for 4 weeks with approximately 500,000 Balb/c or NOD MSCs, or were left untreated. The results show that at 21 weeks of age, the survival rate for normal allogeneic Balb/c MSC-treated group was more than twice the survival rate of the untreated group (PBS, dashed line). In marked contrast, the NOD MSC-treated group had no survivors at 21 weeks. Given that NOD MSCs were not protective in delaying disease onset, there appears to be an intrinsic defect in the stem cell population derived from autoimmune-prone mice.

These results show that development of autoimmune diabetes may be linked to a defect in the MSC pool. Normal allogeneic MSCs can delay disease onset in NOD mice. Furthermore, MSCs can be used as early intervention treatment in diabetes as the treatment was most efficacious in mice that have had disease for only 1-2 weeks. This data suggests that MSCs would be most useful for treatment of new onset diabetes. While not wishing to be bound by any single theory of operability, presumably, these animals undergoing new onset diabetes have a measurable level of functional endogenous beta cells that are able to restore blood glucose levels back to normal once MSCs are administered and control autoimmune T cells.

Example 2

Gene Expression Profiling of Therapeutic MSCs

In the following illustrative examples, a gene expression profile analysis was performed to determine whether normal MSCs and NOD MSCs are intrinsically different with respect to expression of genes possibly involved in MSC mediated immune suppression. Differences in the expression of two genes, Pdcd1Ig1 and CXCL10, were further characterized. Unlike normal MSCs, NOD MSCs did not up-regulate the expression of Pdcd1Ig1, a gene encoding the inhibitory protein PDL1, upon cytokine treatment. MSCs generated from PDL1-deficient mice are less suppressive than their normal counterparts, directly showing that PDL1 expressed by MSCs is involved in suppressing T cell responses. In addition, NOD MSCs, but not normal MSCs, over-express CXCL10 upon cytokine treatment. Further analysis showed that supernatants from NOD MSCs, but not Balb/c MSCs, were able to attract activated T cells. These results show that MSCs from NOD mice are intrinsically different from MSCs from normal mice. NOD MSCs may not protect NOD mice from developing diabetes because NOD MSCs attract autoreactive T cells via over-expression of CXCL10 and fail to suppress these T cells since NOD MSCs do not up-regulate PDL1. The results show that the timely delivery of MSCs to human subjects with early onset diabetes would be beneficial and that expression profile analysis of MSCs identified new potential therapeutic targets for use in the MSC-based treatment of patients with type I diabetes.

Microarray Analysis

Total RNA was isolated from duplicate samples of three independent sets of B/c and B6 MSCs and 2 independent sets of NOD MSCs which had been left untreated or treated for 6 hr with 5 ng/ml recombinant mouse IL1β (R & D Systems). RNA was prepared using standard techniques. Briefly, media was aspirated from the flasks, cold trizol was added and the cells were scraped off, transferred to RNAse free eppendorf tubes and snap frozen. After initial RNA isolation, the RNA was cleaned up using an RNeasy kit (Qiagen). Total RNA was then hybridized to the AFFYMETRIX® mouse whole genome 430 2.0 array. T-tests were performed on data to identify differences in gene expression. Fold changes of 2 or more were considered significantly different.

Flow Cytometry

MSCs were harvested by a 1 minute exposure to 0.05% trypsin-EDTA at 37° C. and then gently scraped. Non-specific staining was blocked using FcR block (BD Biosciences) for 20 minutes on ice. Cells were stained for 30 minutes on ice followed by fixation using 2% paraformaldehyde. A minimum of 10,000 events were acquired using a FACSCanto cytometer and the data was analyzed with FlowJo. MSCs were stained with anti-mouse CD105 (eBiosciences) and anti-mouse CD34, anti-mouse PDL1, anti-mouse PDL2 (BD Biosciences). Appropriate isotype antibodies were used as negative controls.

Quantitative ELISA

CXCL10 was measured in the supernatants of untreated MSCs or those treated with IL1b as described using the mouse CXCL10 DuoSet kit (R & D Systems) following the manufacturer's instructions. For each sample, 200 ul of neat supernatant was added to the top well with 1:2 dilutions down the plate starting with well 2.

CFSE Staining

Splenocytes were washed in PBS then re-suspended in PBS. A 1:1 volume of CFSE (Molecular Probes) at 10 uM in PBS was added and the cells incubated for 5 minutes in the dark. The reaction was stopped by adding 1:1 volume of 100% FBS for 1 minute followed by several washes in RPMI+10% FBS.

Proliferation Assay

Two million CFSE labeled Balb/c splenocytes were stimulated for 4 days with 2 ug/ml soluble anti-mouse CD3ε or hamster IgG1 (BD Biosciences) in the absence or presence of 25,000 MSCs. On the day of culture initiation, splenocytes, MSCs, and stimulating reagents were added at the same time. On the fourth day, the CFSE profile of the non-adherent cells was analyzed by flow cytometry.

Adenoviral Transduction

NOD MSCs were infected with an adenoviral vector encoding mouse membrane PDL1 (Ad.mPDL1) at an MOI of 1000. The cells were incubated with Ad.mPDL1 for 4 hours in high glucose DMEM without FBS. The cells were washed twice with DMEM then complete media was added back. Twenty-four hours later the cells were harvested by 1 minute trypsin-EDTA incubation and injected. The mice were injected once a week for 4 weeks as described above, and the membrane expression of PDL1 was assessed by flow cytometry each week.

Autoimmune-Prone NOD Mouse MSCs Differ from Normal MSCs

The intrinsic differences in MSCs derived from autoimmune-prone NOD mice were compared to MSCs derived from normal mice by gene expression profiling. NOD mice spontaneously develop an autoimmune disease that resembles type 1 diabetes in humans (Kikutani and Makino, Adv. Immunol. 51:285-322 (1992)), and multiple chromosomal abnormalities have been identified which contribute to disease development. Although defects in multiple cell types, such as macrophages, dendritic cells, and T cells, have been described in these mice, defects in the adult stem cell population have not been described. Accordingly, the contribution of adult stem cell genotype to disease development was investigated.

Figures 4A, 4B:
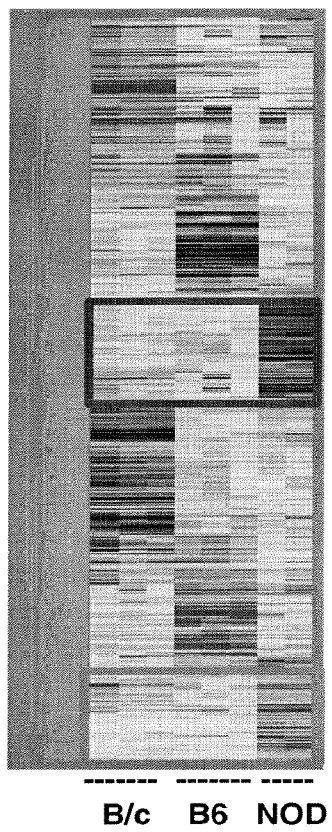
FIG. 4A is a "heat map" expression profile showing the various up-regulated and down-regulated genes in NOD MSCs after IL1β treatment.
FIG. 4B is a summary of the genes differentially expressed in NOD autoimmune-prone MSCs as compared to normal MSCs following IL1β treatment.

A gene expression profile analysis using microarray technology was performed to further investigate the mechanism by which B/c MSCs afford protection from diabetes while NOD MSCs do not (and may even accelerate diabetes development). This analysis was performed on MSCs derived from normal and pre-diabetic NOD mice. RNA harvested from untreated as well as IL-1β treated MSCs was analyzed. Multiple differences in gene expression between normal and autoimmune-prone MSCs were identified. FIG. 4A shows a "heat map" in which differences in IL-1β treated RNA from NOD MSCs vs. IL-1β treated normal B6 and B/C MSCs are boxed. The dark gray box (top) represents genes which are down-regulated whereas the genes boxed in light gray (bottom) are up-regulated. FIG. 4B lists the top genes of particular interest that were highly differentially expressed in IL-1β-treated NOD MSCs as compared to normal MSCs. A dash means the gene was not up-regulated and an up arrow means the gene was up-regulated.

Normal MSCs Up-Regulate PD-L1 upon Inflammation Stimulation

Figure 5A:
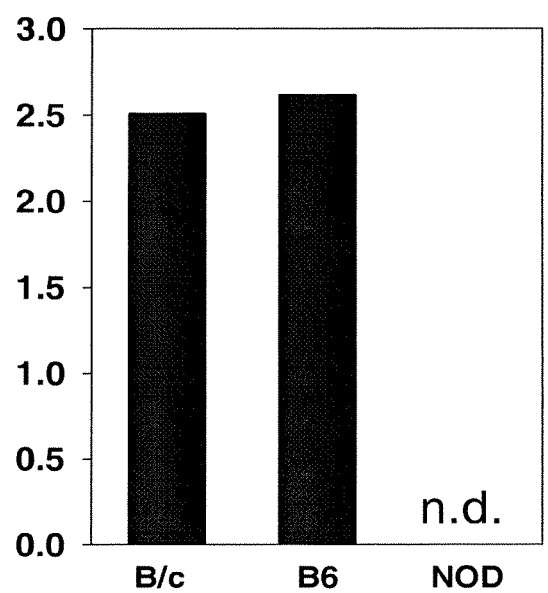
FIG. 5A is a graphical representation of experiments demonstrating that normal (Balb/c or C57BL/6) MSCs, but not NOD MSCs, up-regulated PD-L1 in response to IL1β treatment.
Figure 5B:
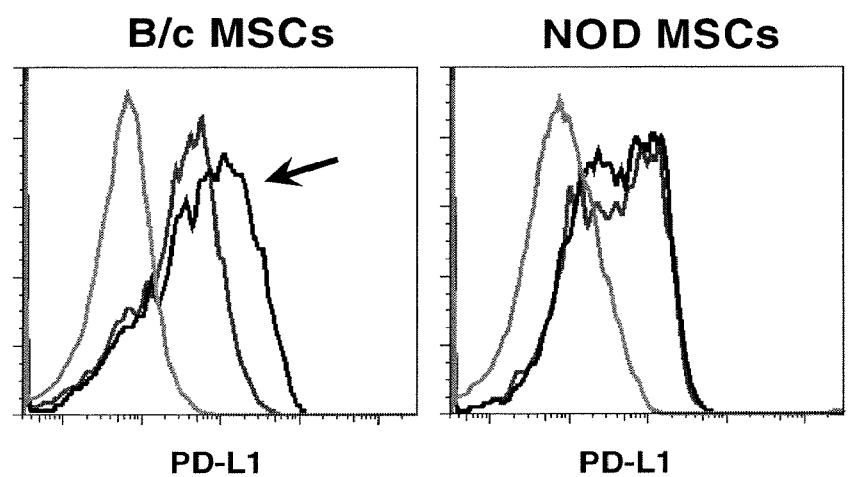
FIG. 5B is a flow cytometry analysis of PD-L1 protein on the surface of normal (Balb/c) and diabetic (NOD) MSCs treated with IL1β.

The microarray gene analysis results showed that NOD MSCs did not up-regulate the negative co-stimulatory molecule PD-L1 upon IL-1β stimulation (FIG. 5A). While the PD-L1/PD1 pathway has been implicated in T cell regulation in autoimmune diseases (Okazaki and Honjo, Trends Immunol. 27:195-201 (2006)) and diabetes (Ansari, et al., J. Exp. Med. 198:63-9 (2003)), further studies focused on this molecule and the PD-1 pathway were required to understand its role in autoimmune disease progression. FAQS data confirmed the microarray results at the protein level and showed that NOD MSCs did not up-regulate the co-stimulatory molecule PD-L1 upon IL-1β stimulation compared to normal B6 MSCs. (FIG. 5B). This data indicates that MSCs derived from autoimmune-prone mice have a dysregulation in the PD-1 negative co-stimulatory pathway and do not possess the immunosuppressive function necessary to inhibit T cell proliferation.

In further detail, FIGS. 5A and 5B show that normal Balb/c and C57BL/6 MSCs, but not NOD MSCs, up-regulate PD-L1 in response to IL-1β. FIG. 5A shows the fold change in mRNA expression of the Pdcd1lg1 gene, encoding PD-L1, for Balb/c (left bar), C57BL/6 (middle bar), and NOD (right bar). MSCs were determined by dividing the raw expression data for the gene from IL-1β treated samples divided by the raw value of the untreated samples for each strain (n.d. indicates "not detected"). FIG. 5B shows the flow cytometry analysis of PD-L1 protein on the surface of Balb/c and NOD MSCs cultured in the presence or absence of IL-1β for 6 hr. The black line (arrow) represents cells treated with IL-1β for 6 hr, the dark gray line represents untreated MSCs and the light gray line represents untreated cells stained with the appropriate isotype control antibody.

Figure 6:
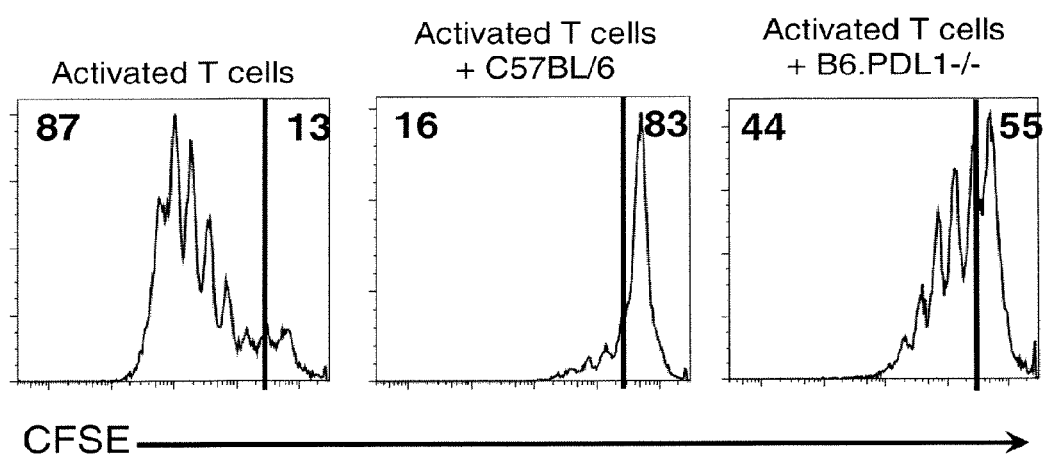
FIG. 6 is a graphical representation of experiments demonstrating that MSCs lacking PD-L1 expression demonstrate a reduced ability to inhibit T cell proliferation.

Reduced Ability of MSCs Lacking PD-L1 Expression to Inhibit T Cell Proliferation The role of PD-L1 in mediating suppression of T cell proliferation by MSCs was further investigated. MSCs were derived from the bone marrow of PD-L1 deficient mice (Latchman, et al., Proc. Natl. Acad. Sci. USA 101:10691-96 (2004)). Wildtype B/6 MSCs and B/6−/− PD-L1 MSCs were cultured together with CD3 activated B/C splenocytes in a mixed lymphocyte reaction (MLR). In FIG. 6, the left panel depicts 87% of the activated T cells proliferated. Addition of the wildtype B6 MSCs to the MLR suppressed this T cell proliferation over five-fold to 16% (middle panel), whereas addition of B6 PD-L1−/− MSCs resulted in less than 2-fold suppression of T cell proliferation (right panel). Increasing numbers of B6 PD-L1−/− MSCs were not able to further suppress T cell proliferation. This data shows that PD-L1 is an important mediator in the MSC-mediated suppression of lymphocyte proliferation, because the absence of PD-L1 ligand on the cell surface of the null MSCs prevents binding to the PD-1 receptor, and thus prevents the activation of the negative co-stimulatory pathway in the T cells allowing T cell proliferation.

FIG. 6 shows that the ability of MSCs to inhibit T cell proliferation is reduced when MSCs lack PD-L1 expression. In further detail, FIG. 6 shows flow cytometry analysis of CFSE labeled B/c splenocytes cultured with anti-mouse CD3ε antibody alone (left panel) or together with 25,000 B6 (middle panel) or B6.PD-L1−/− (right panel) MSCs. The thick vertical line demarcates proliferating cells (to the left of the line) from non-proliferating cells (to the right of the line) and the numbers represent the percentage of cells in these gates within the lymphocyte compartment.

Taken together, this data supports the observation that autoimmune-prone MSCs, which lack the ability to up-regulate PD-L1 on their cell surface, cannot offer disease protection when delivered prophylactically to NOD mice.

NOD MSCs Engineered to Over-Express PD-L1 Delay Diabetes

Figure 7A:
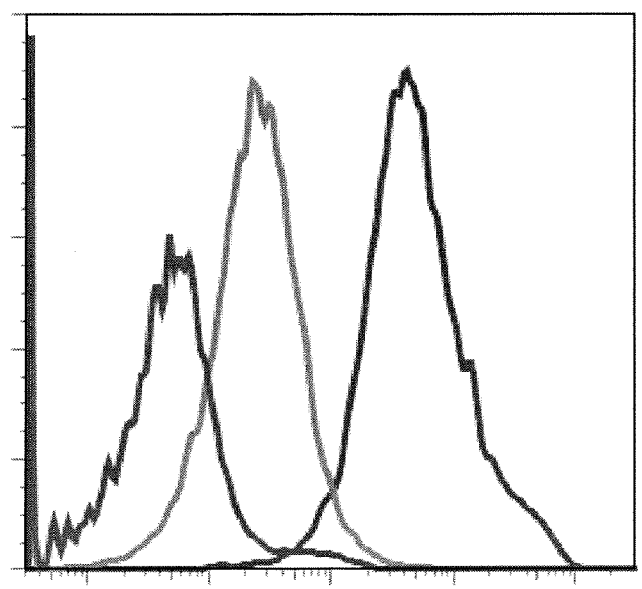
FIG. 7A is a flow cytometry analysis of PD-L1 expression on the surface of NOD MSCs infected with adenoviral vector encoding mouse membrane PD-L1 (Ad.mPD-L1).
Figure 7B:
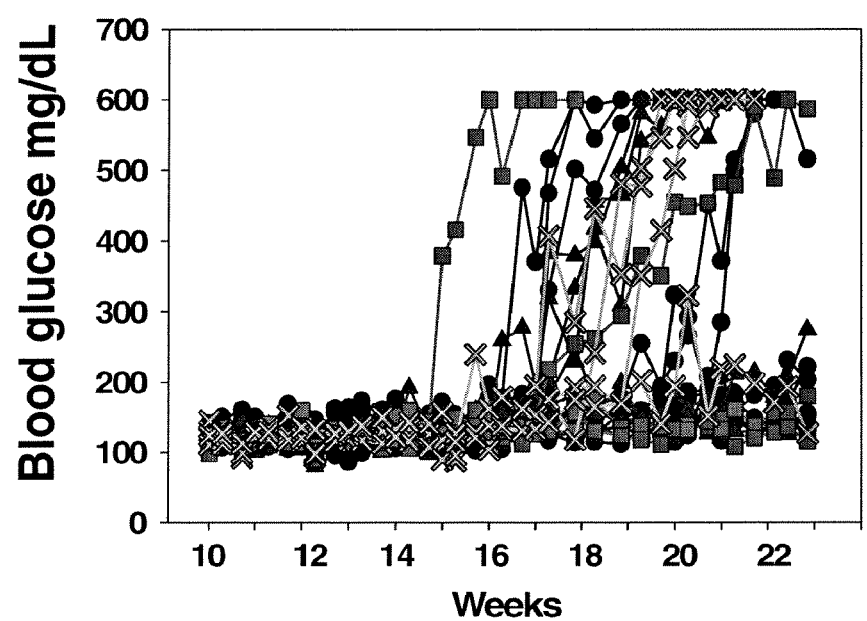
FIG. 7B is a graphical representation of experiments demonstrating that NOD MSCs engineered to over-express PD-L1 delay onset of diabetes in NOD mice.

The role, of PD-L1 in mediating MSC immune suppression was further analyzed by engineering NOD MSCs to over-express PD-L1 using an adenoviral vector encoding mouse membrane bound PD-L1 (Ad.mPD-L1). FIG. 7A shows FACS analysis of PD-L1 cell surface expression on Ad.mPD-L1 infected NOD MSCs stained with an isotype control, vs. uninfected NOD MSCs, vs. Ad.mPD-L1 infected MSCs stained with an anti-PD-L1 monoclonal antibody, respectively. To elucidate the role of PD-L1 as the underlying pathway conveying therapeutic potential of MSCs for the treatment of diabetes, pre-diabetic NOD mice were again treated with normal allogeneic Balb/c MSCs (wildtype), NOD MSCs (derived from 10-week old, pre-diabetic NOD mice), or Ad.mPD-L1 engineered NOD MSCs once a week for 4 weeks and disease development was monitored by measuring blood glucose levels. The data confirmed that wildtype NOD MSCs did not confer protection to disease onset as these cohorts developed disease starting at 15 weeks of age. In contrast, NOD MSCs engineered to express PD-L1 on their cells surface conferred protection by delaying disease onset to 17-19 weeks of age similar to normal B/C MSCs (FIG. 7B).

In further detail, FIG. 7A shows flow cytometry analysis of PD-L1 expression on the surface of NOD MSCs infected with adenoviral vector encoding mouse membrane PD-L1 (Ad-.mPD-L1). Uninfected (light grey line, center peak) or Ad.mPD-L1 infected (grey line, right peak) NOD MSCs were stained with an antibody to PD-L1. The dark line (left peak) represents Ad.mPD-L1 infected NOD MSCs stained with isotype control antibody. FIG. 7B shows blood glucose values over time from NOD mice left untreated (circles, black line) or administered 500,000 uninfected Balb/c MSCs (triangles), uninfected NOD MSCs (squares, grey line), or Ad.mPD-L1 infected NOD MSCs (X's, light grey line) starting at 10 weeks of age. Collectively, FIGS. 7A and 7B demonstrate that NOD MSCs engineered to over-express PD-L1 delay diabetes.

This data shows that the intrinsic PD-L1 defect resulting in lack of inducible expression on autoimmune-prone MSCs leading to early onset disease can be completely reversed by restoring PD-L1 expression to these cells. These results demonstrate that the expression of the negative co-stimulatory molecule PD-L1 is critical for the innate immunosuppressive function of MSCs. In addition, lack of expression of this molecule on the MSC population may contribute to disease development due to lack of T cell suppression.

Construction of PD-L1-Fc Fusion Protein (PD-1-PDL-1/PDL-2 Agonist)

PD-L1 Fc fusion protein was created by fusing the DNA sequence encoding the full length mouse PD-L1 protein to the DNA sequence encoding the Fc portion of human IgG1. The sequence for the Fc portion encodes the $C_H2$ and $C_H3C$-region domains of IgG1 and 7 out of 12 amino acids that make up the hinge region most proximal to the sequence encoding the $C_H2$ domain. The 7 amino acids include the cysteine residues which make the covalent disulfide bonds involved in dimer formation. The PD-L1 Fc protein is a dimer composed of 2 PD-L1-Fc chains. Being a dimer, one PD-L1 Fc protein theoretically should bind 2 receptor molecules.

NOD MSCs, but not Normal MSCs, Over-Express CXCL 10

Figure 8A:
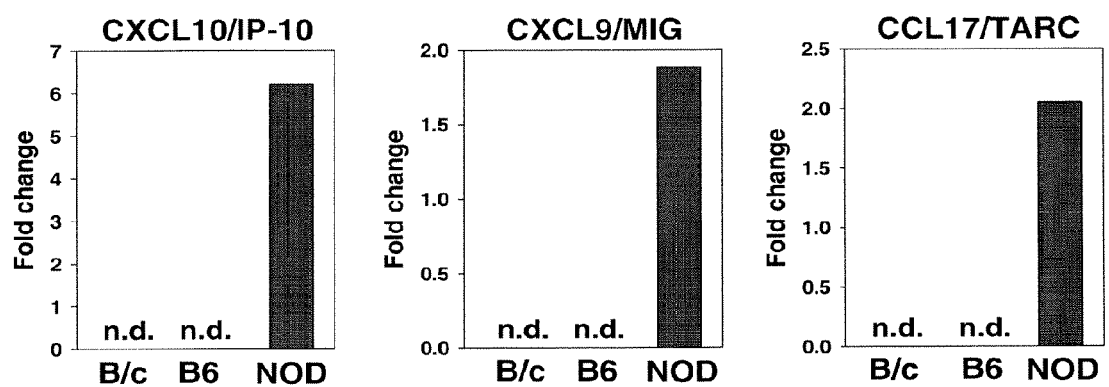
FIG. 8A is a graphical representation of experiments demonstrating that NOD MSCs, but not normal (Balb/c or C57BL/6) MSCs, over-express CXCL10-CXCR3 pathway genes.
Figure 8B:
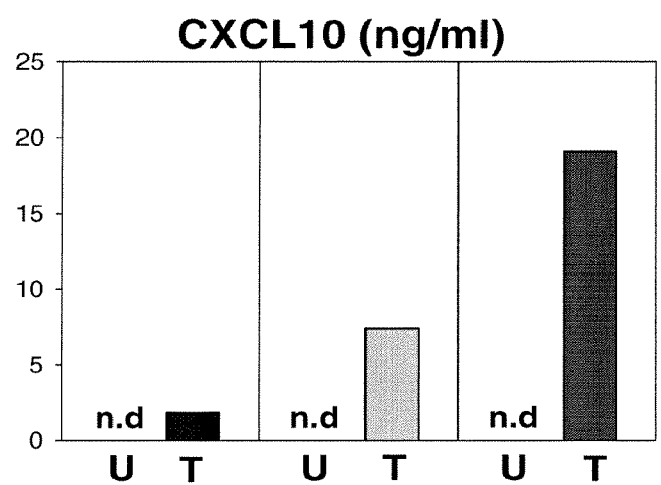
FIG. 8B is a graphical representation of experiments demonstrating that NOD MSCs express CXCL10 in response to IFN-γ treatment.

Further differences between autoimmune-prone NOD MSCs and normal MSCs were evident in the gene expression level of CXCL10/CXCR3 chemokine pathway. FIG. 8A shows that NOD MSCs over-express the chemokine CXCL10 6-fold over Balb/c and B6 MSCs in response to IL-1β treatment, respectively. In addition, CXCL9 and CCR17 chemokines are up-regulated 1.5-2.0 fold over normal MSCs in NOD MSCs. The over-expression of CXCL10 gene expression in response to inflammatory cytokines by NOD MSCs was confirmed on the protein level by ELISA (FIG. 8B).

In further detail, FIG. 8A shows the fold change in CXCL10, CXCL9, and CCL17 mRNA expression of IL-1β treated to untreated Balb/c (left bar), C57BL/6 (middle bar), and NOD (right bar) MSC samples. FIG. 8B shows that supernatants from Balb/c (black bar, left panel), C57BL/6 (light grey bar, center panel), and NOD (grey bar, right panel) MSCs incubated for 6 hours+/−IFN-γ were analyzed for CXCL10 protein via quantitative ELISA (U=untreated, T=IFN-γ treated, and n.d.=not detected). Therefore, FIG. 8 demonstrates that NOD MSCs, but not Balb/c and C57BL/6 MSCs, over-express CXCL10.

This data confirmed that NOD MSCs secrete higher levels of the chemokine CXCL10 in response to the pro-inflammatory cytokine IFN-γ. Given that CXCL10 is an important chemokine for T cell trafficking, this data further suggests that autoimmune-prone MSCs may further exacerbate disease by secreting CXCL10, which may recruit autoreactive T cells.

Anti-CXCL 10 Antibody Treatment Delays Diabetes Onset

The results show that NOD MSCs secrete higher levels of the chemokine CXCL10 in response to an inflammatory stimulus. Based on this data, activated T cells would be expected to preferentially migrate towards supernatants collected from stimulated NOD MSCs cultures compared to supernatants collected from normal MSCs in an in vitro chemotaxis assay.

Based on the data showing that NOD MSCs overexpress CXCL10 and other chemokines in this pathway and the observation that delivery of NOD MSCs to pre-diabetic NOD mice contributes to disease development, in vivo administration of an anti-CXCL10 antibody would be expected to delay disease development by blocking additional recruitment of autoreactive T cells that lead to disease development.

These results demonstrate that the MSCs from NOD mice are intrinsically different from normal and may attract alloreactive T cells by secretion of CXCL10. In addition, NOD MSCs may not functionally suppress these immune cells due to a decrease in PD-L1 expression, thereby contributing to auto-immunity and explaining disease acceleration after systemic treatment with NOD MSCs. This data shows that autoimmune-prone MSCs are defective in PD-L1 expression and link this pathway and a defect in the stem cell pool to the development of autoimmune diabetes.

Example 3

Further Analysis of MSC Treatment for New Onset Type I Diabetes

To further demonstrate the effectiveness of MSCs on the treatment or prevention of diabetes, the MSC-mediated suppression of T cell responses and inhibition of key inflammatory mediators, such as TNFα, were further analyzed. Allogeneic murine MSCs were administered to NOD mice, either prior to (preventive protocol) or at the time of disease onset (therapeutic protocol). Prophylactic delivery of allogeneic MSCs to pre-diabetic NOD mice delayed the onset of disease. Therapeutic treatment at the time of disease onset was effective in reversing disease, as measured by restoration of blood glucose levels to the normal range. MSCs were shown to traffic to the pancreatic draining lymph node and spleen in pre-diabetic and diabetic mice, implying that MSCs modulated the autoreactive response at these sites. These findings further demonstrate that MSCs can effectively alter the autoimmune response and lead to the amelioration of an ongoing diabetic condition, in addition to being effective in delaying the onset of a developing diabetic condition.

Animals

MSCs were generated from 6-8 week old female mice (Balb/c, C57BL/6, C57BL/6-Tg (UBC-GFP) 30Scha/J) purchased from the Jackson Laboratory (Bar Harbor, Me.). For the diabetes studies, NOD/LtJ mice (Jackson Laboratory) were maintained under pathogen-free conditions and screened for glycosuria using an ACCU-CHEK Compact Plus Blood Glucose Meter (Roche, Indianapolis, Ind.) by tail vein puncture three times a week starting at 10 weeks of age. Mice were deemed diabetic when blood glucose measured above 250 mg/dL for three consecutive days.

Cell Therapy

For prevention studies, 10 week old pre-diabetic female NOD mice were injected with 500,000 Balb/c MSCs i.v. once a week for 4 weeks. For reversal studies, mice were enrolled the day after the third blood glucose reading >250 mg/dL and administered Balb/c MSCs ($1 \times 10^6$ i.v. twice a week for 4 weeks) within 7 days. Once enrolled, hyperglycemic mice (blood glucose >250 mg/dL) received daily insulin glargine (Sonafi Aventis, Bridgewater, N.J.) injections except mice therapeutically treated with MSCs who were not given insulin unless blood glucose rose above 250 mg/dL. MSC treated mice with blood glucose $\leq$250 mg/dL for an extended time were considered responders. Mice were observed for up to 60 days post initial treatment.

MSC Generation and Propagation

Human MSCs were generated from BM mononuclear cells obtained from whole BM aspirates (Lonza, Walkersville, Md.) by density gradient centrifugation as described previously (Lodie, et al., *Tissue Eng.* 8:739-51 (2002)). Mouse MSCs were generated from BM cells flushed from both femurs and tibias of 10-30 mice with high glucose DMEM media (DMEM-H; Invitrogen, Carlsbad, Calif.). Flushed cells were pooled, treated to lyse red blood cells, and plated at $10-12 \times 10^6$ cells per 25 cm$^2$ tissue culture flask in DMEM-H containing 10% FBS, 1× penicillin/streptomycin, and 2 mM L-glutamine. 3-5 days after initial plating, the media containing non-adherent cells was removed and replaced. On day 7, the adherent cells were harvested by trypsin-EDTA (Invitrogen) treatment with gentle scraping and pooled down. Cells were expanded every 3-4 days once 80-90% confluent for up to 8 passages. MSCs from multiple harvests were cultured at 37° C. in 5% $CO_2$ and used in experiments.

Cytokine Analysis

Cytokines were measured in culture supernatants or plasma using the human Th1/Th2 or mouse inflammation CBA kit (BD Biosciences, San Jose, Calif.), respectively, following the manufacturer's instructions.

MSC Tracking

One million MSCs generated from GFP transgenic C57BL/6 mice were delivered i.p. to non-diabetic and diabetic NOD mice and 4 days later organs were harvested, homogenized in trizol, and snap frozen. RNA was isolated using standard techniques and GFP expression was analyzed by quantitative PCR using the following GFP primers: 5'-CTGCTGCCCGACAACCAC-3' (SEQ ID NO: 1) (forward) and 5'-ACCATGTGATCGCGCTTCTC-3' (SEQ ID NO: 2) (reverse) (Integrated DNA Technologies, Coralville, Iowa). The relative GFP copy number in each tissue was extrapolated using various amounts of plasmid containing a known number of GFP genes.

Dendritic Cell (DC) Preparation

Normal donor PBMCs (HemaCare Corporation, Van Nuys, Calif.) were plated at $5.5 \times 10^6$ cells/150 cm$^2$ flask in RPMI 1640 (Invitrogen) containing 5% huAB (Sigma, St. Louis, Mo.) for 1-2 hrs. Non-adherent cells were removed and adherent cells were cultured for 6-7 days in media containing human recombinant IL-4 (20 ng/ml) and GMCSF (100 ng/ml; Peprotech Inc., Rocky Hill, N.J.) then phenotyped by flow cytometry and cryopreserved for later use.

Proliferation Assay

For human MSC assays, PBMCs (400,000/well) or purified CD3+ cells (100,000/well) were stimulated with anti-CD3/CD28 beads (1 bead:1 PBMC; Invitrogen) or allogeneic DCs (100,000/well)±human MSCs or HUVECs (ATCC, Manassas, Va.), as described in the figures, respectively. The MSCs were allogeneic to the T cells/PBMCs and to the DCs.

For mouse MSC assays, splenocytes (500,000/well) were stimulated with 2 ug/ml anti-mouse CD3e (BD Biosciences) ±MSCs as described in the figures. The splenocytes, MSCs and stimulating reagents were added at culture initiation.

Proliferation was measured after incubation with 1 µCi $^3$H thymidine (Perkin Elmer, Boston, Mass.) for the last 18 hours of culture for each condition in triplicate.

Glucose Tolerance Testing

The evening before the glucose challenge, non-fasting blood glucose was monitored and insulin treatment of diabetic animals was withheld. Mice were fasted for 12 hours before D-glucose (20%; Sigma) at 2 mg/g body weight was injected i.p. Blood glucose was measured before and 15, 30, 60, and 120 minutes after the injection.

MSCs Suppress T Cell Responses

Figure 9A:
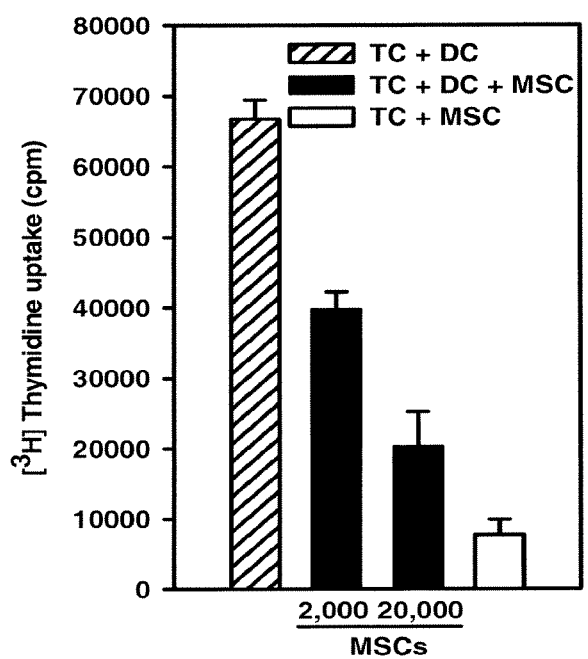
FIG. 9A is a graphical representation of experiments demonstrating the inhibition by different doses of human MSCs (MSC) of human T cell (TC) proliferation induced by human allogeneic dendritic cells (DC), as measured by tritiated thymidine incorporation after 6 days.

The MSCs were subjected to culture conditions under which they have previously been shown to differentiate into fat, cartilage, and bone. To confirm that the MSCs were immunomodulatory, the ability of MSCs to suppress T cell responses in vitro was further assessed. T cell proliferation in response to allogeneic DCs was inhibited by MSC addition to the cultures in a dose-dependent fashion (FIG. 9A). The immunomodulatory activity is a general characteristic of MSCs because MSCs from multiple donors suppress T cell proliferation (FIG. 9B), whereas HUVECs, a human endothelial cell line, do not (FIG. 9C). The MSCs cause an arrest of T cell proliferation, and not the induction of T cell apoptosis, because the percentage of cells in MSC treated cultures did not decrease and no increase in propidium iodine/annexin V staining was observed. The observation that MSCs alone do not activate T cells is consistent with the fact that, in contrast to DCs, MCS under these conditions express little to no HLA class II or co-stimulatory molecules such as CD80 and CD86 (Jones et al., *J. Immunol.* 179:2824-31 (2007)).

Figure 9B:
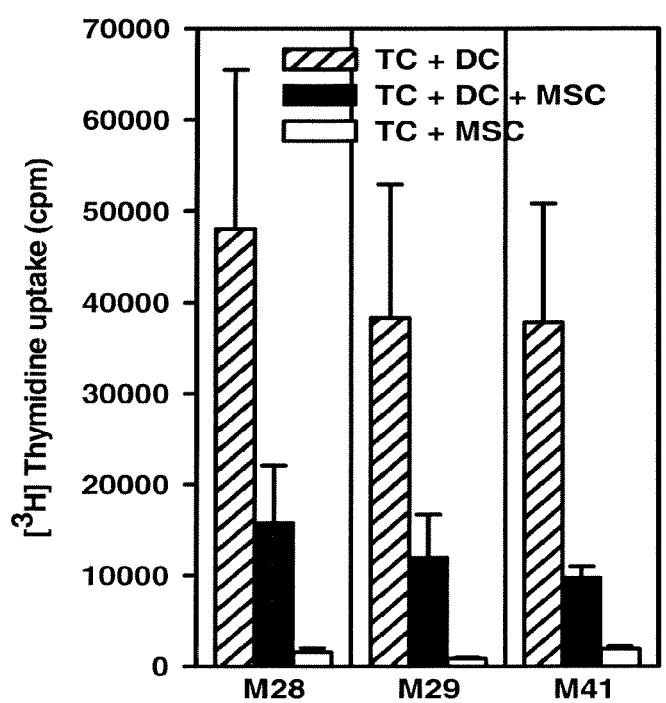
FIG. 9B is a graphical representation of experiments demonstrating the inhibition by human MSCs (MSC) from different donors (M28, M29 and M41).
Figure 9C:
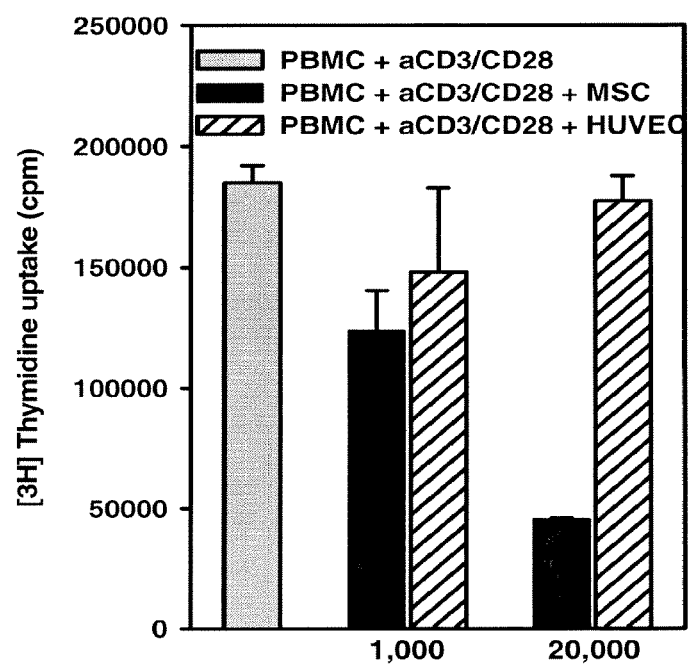
FIG. 9C is a graphical representation of experiments demonstrating the inhibition by different doses of human MSCs (MSC) or human umbilical vein endothelial cells (HUVECs) of human peripheral blood mononuclear cell (PBMC) proliferation induced by anti-CD3/anti-CD28 coated beads, as measured by tritiated thymidine incorporation after 5 days.

In further detail, FIGS. 9A to 9C show that MSCs inhibit T cell proliferation. FIG. 9A shows purified human T cells (TC) cultured with human allogeneic dendritic cells (DC) with or without the indicated doses of third party human MSCs (MSC) for 6 days. FIG. 9B shows TCs cultured with allogeneic DC alone or together with 20,000 MSC from three different donors (donors M28, M29 and M41) for 5 days. FIG. 9C shows PBMCs cultured with anti-CD3/anti-CD28 beads with or without the indicated doses of human MSCs, or the control HUVEC line, for 3 days. Cell proliferation was measured by tritiated thymidine incorporation.

MSCs Modulate TNFα and IL10 Expression

Figure 10:
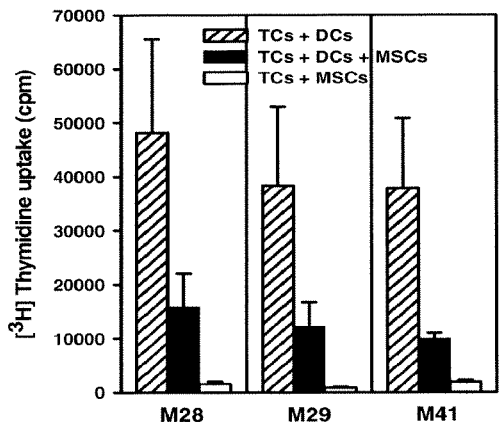
FIG. 10 is a graphical representation of experiments demonstrating that MSCs modulate cytokines in vitro as shown by TNFα (middle panel) and IL10 (bottom panel) levels following T cell activation by human peripheral blood mononuclear cells (PBMC) (proliferation induced by human allogeneic dendritic cells (DC), as measured by tritiated thymidine incorporation, is shown in the top panel).
Figure 10:
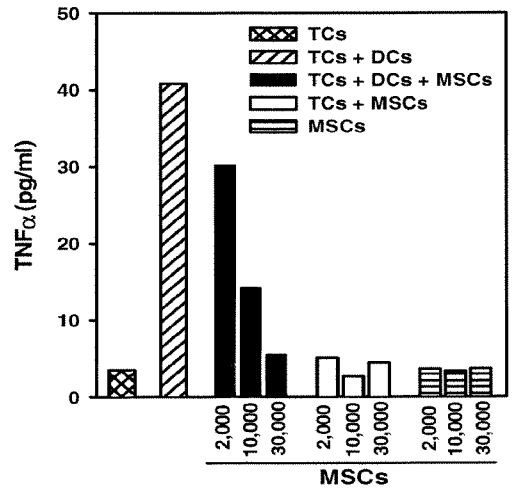
Figure 10:
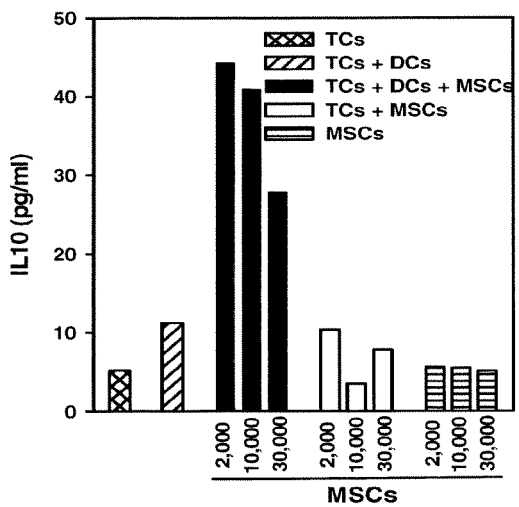

To further assess the effect of MSCs on cytokine secretion, supernatants from MSC-treated cultures were analyzed for the presence of cytokines. TNFα and IL10 were elevated in supernatants from T cell/DC cultures but TNFα levels decreased and IL10 levels increased when MSCs were present (FIG. 10). In further detail, FIG. 10 shows the results of experiments demonstrating that MSCs modulate cytokines in vitro. A proliferation assay was performed as above (top panel) and supernatants harvested at the end of the assay were tested for the presence of TNFα (middle panel) and IL10 (bottom panel) by cytometric bead array. This pattern was observed whether the supernatants were taken early or late in the culture period. TNFα is a pro-inflammatory cytokine that is secreted by activated T cells and IL10 is a T cell derived anti-inflammatory cytokine. These results show that MSCs shift the cytokine response from pro-inflammatory to anti-inflammatory. MSC-mediated suppression of T cell proliferation is reduced when neutralizing anti-IL10 antibodies are added to the cultures (Rasmusson, et al. *Exp. Cell. Res.* 305: 33-41 (2005)), suggesting that IL-10 contributes to MSC immunomodulation.

MSCs Modulate TNFα Expression In Vivo

Figure 11A:
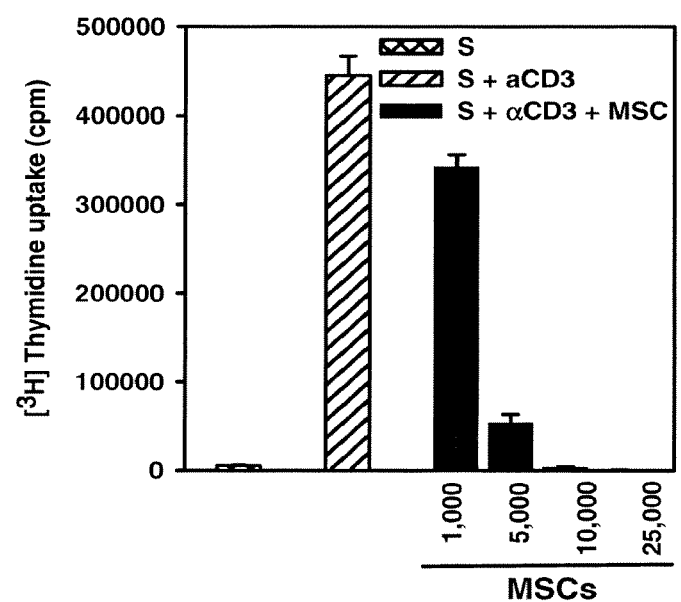
FIG. 11A is a graphical representation of experiments demonstrating that mouse MSCs inhibit T cell proliferation in vitro.

The mechanism by which MSCs down-regulate the TNFα-mediated inflammatory response was further assessed in vivo. First, mouse MSCs were generated to confirm that murine and human MSCs are phenotypically and functionally similar. Like human MSCs, BM-derived MSCs from Balb/c and C57BL/6 mice expressed typical MSC surface markers such as CD44, CD105, and CD73, but lacked hematopoietic markers like CD34. Mouse MSCs functioned like human MSCs in that mouse MSCs differentiated into multiple mesenchymal lineages and suppressed T cell proliferation in vitro in a dose dependent fashion (FIG. 11A).

Figure 11B:
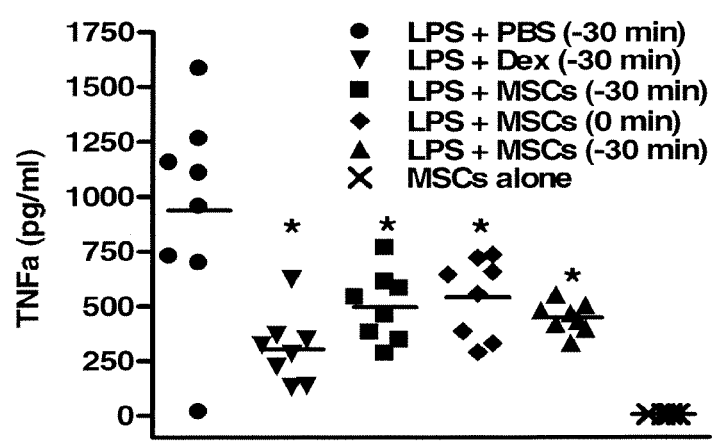
FIG. 11B is a graphical representation of experiments demonstrating that mouse MSCs dampen TNFα in vivo.

To further show that MSCs modulate TNFα in vivo, MSCs were delivered to mice challenged with lipopolysaccharide (LPS). LPS injection results in a cytokine storm characterized by rapid TNFα up-regulation. TNFα was significantly reduced in the plasma of mice receiving MSCs regardless of whether the MSCs were delivered 30 minutes prior to, at the same time as, or 30 minutes post LPS injection (FIG. 11B). TNFα reduction by MSCs was similar to the reduction caused by dexamethasone treatment. The finding that MSCs dampen the TNFα response shows that MSCs can be anti-inflammatory. In further detail, FIG. 11A shows the proliferation of Balb/c spleen cells (S) cultured for 3 days with soluble anti-CD3 antibody (aCD3) with or without the indicated doses of C57BL/6 MSCs. FIG. 11B shows the results of an experiment in which C57BL/6 mice were administered 5 µg LPS i.p. and treated with PBS i.p. (circle), 40 ug dexamethasone i.p. (inverted triangle), or 500,000 C57BL/6 MSCs i.v., which were delivered 30 minutes before (squares), at the same time (diamond), or 30 minutes after (triangle) LPS injection. As a control, a group of mice were given MSCs alone without LPS treatment (cross). The asterisks represent p values <0.01 when comparing the PBS treated mice to those treated with dexamethasone or MSCs using a Dunnett's multiple comparison test.

MSCs Delay Diabetes Onset in NOD Mice

Figure 12A:
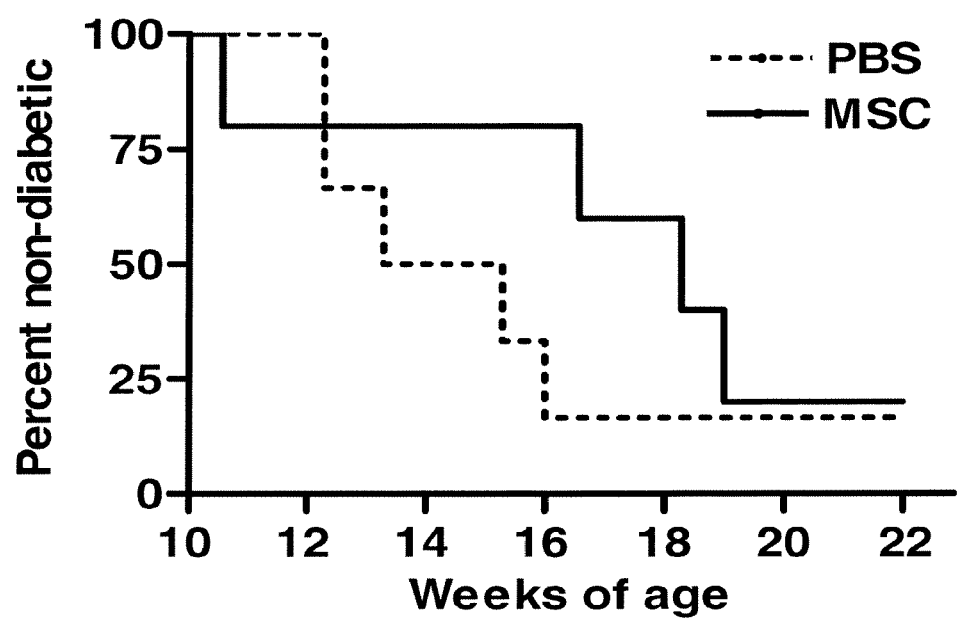
FIG. 12A is a graphical representation of experiments demonstrating the delay of diabetes onset by administration of allogeneic MSCs.
Figure 12B:
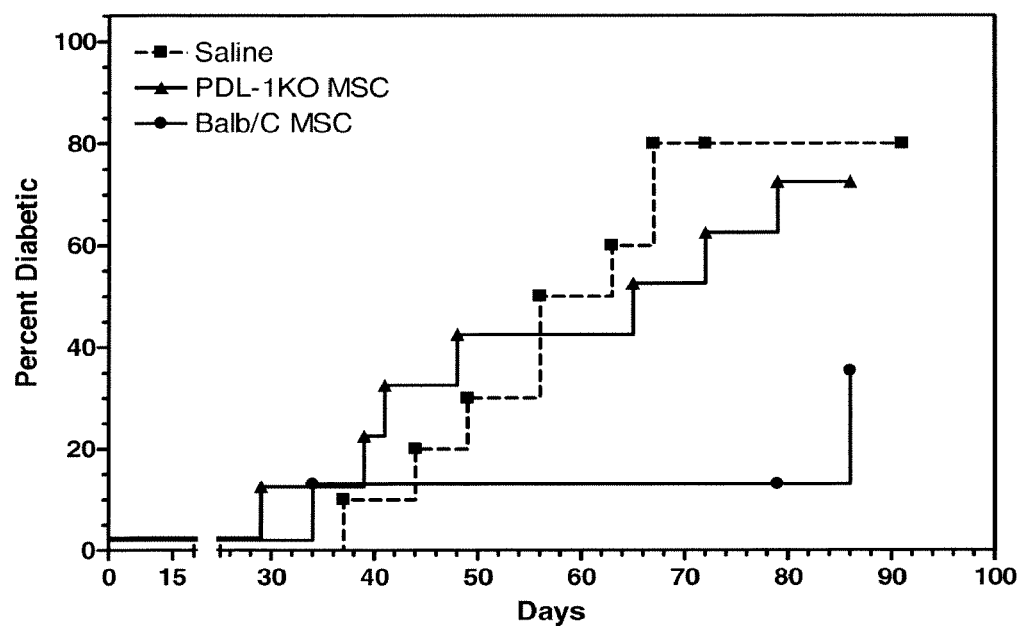
FIG. 12B is a graphical representation of experiments that PDL-1 knock-out MSCs do not significantly delay the onset of diabetes in NOD mice.

Knowing that MSCs suppress T cell responses in vitro and dampen the TNFα response in vivo, allogeneic MSCs were delivered to pre-diabetic NOD animals to determine whether systemic delivery could alter the course of disease. Type I diabetes results from the autoimmune destruction of beta cells by T cells and TNFα is an early inflammatory mediator of disease and is thought to be directly toxic to beta cells (La Cava, et al. *Curr. Dir. Autoimmun.* 1:56-71 (1999); Bach, *J. Autoimmun.* 8:439-63 (1995)). To test the effect of MSCs in NOD mice, pre-diabetic NOD mice were administered Balb/c MSCs or PBS. By the end of the study, the number of hyperglycemic mice in the MSC treated and control groups were similar. At 22 weeks of age, 4 of 5 MSC treated mice and 5 of 6 PBS treated mice had developed diabetes (FIG. 12A); however, disease onset was delayed by 4 weeks with MSC treatment. Pre-diabetic NOD mice were administered PBS or 500,000 allogeneic Balb/c MSCs i.v. once a week for 4 weeks starting at 10 weeks of age. Blood glucose values for individual mice were monitored and plotted to assess development of disease. The data is depicted as percent of non-diabetic mice based on these blood glucose values. Results are representative of at least 3 independent experiments. This data shows that MSCs can delay the development of hyperglycemia in NOD mice. In contrast, MSCs derived from PDL-1 knock-out mice did not significantly delay the onset of diabetes in NOD mice, demonstrating that PDL-1 is critical to the diabetes therapeutic potential of the allogeneic MSCs (FIG. 12B).

MSCs can Reverse Established Disease in NOD Mice.

To further demonstrate the utility of treating hyperglycemia with MSCs, allogeneic Balb/c MSCs were delivered therapeutically after disease onset. Although many agents can prevent disease development when given during the pre-diabetic phase, few have been shown to reverse disease effectively in the diabetic setting (Shoda, et al. *Immunity* 23:115-26 (2005)). Diabetes is a progressive and overt disease and is reported not to occur until the majority of islets have been destroyed (Yoon, et al. *Autoimmunity* 27:109-22 (1998)). New onset patients are an important population because it is believed that some beta cell function is still present in these patients. To reverse diabetes in new onset patients, an ideal therapy would dampen the autoimmunity and inflammatory responses and give support to the surviving beta cells. Theoretically, MSCs could provide these functions because MSCs dampen T cell responses and inflammatory responses and the primary function of MSCs in the BM is to provide support for developing cells. Accordingly, exogenously administered MSCs may function similarly by supporting beta cells in the pancreas.

Figure 13A:
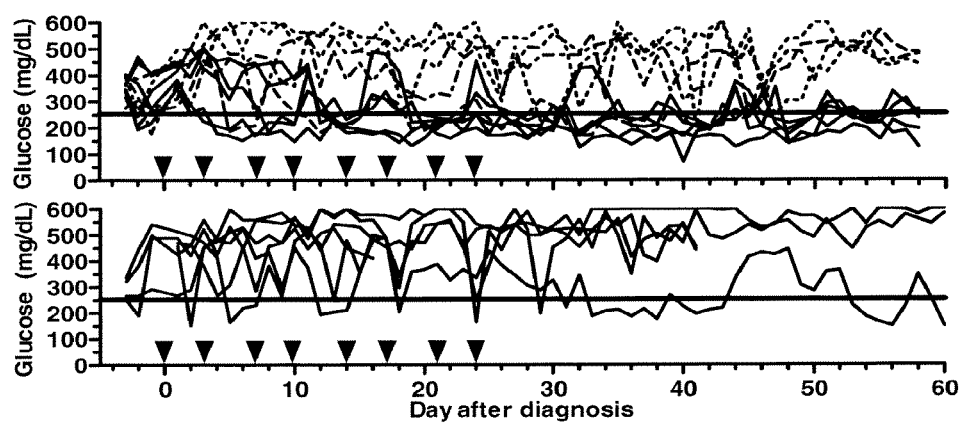
FIG. 13A is a graphical representation of experiments demonstrating the reversal of diabetes with allogeneic MSCs, as demonstrated by blood glucose levels following administration of $1 \times 10^6$ allogeneic Balb/c MSCs (top panel), but no reversal of diabetes with PBS (bottom panel) administered twice weekly (black arrowheads).

To further demonstrate that MSCs can reverse hyperglycemia, MSCs were delivered to newly diabetic NOD mice. Mice with persistent glucose levels <250 mg/dL were considered to be responders. Six out of ten mice reversed long term when given MSCs without any other therapy compared to one out of six mice given PBS and insulin daily (FIG. 13A). FIG. 13A shows the reversal of diabetes with allogeneic MSCs in newly diabetic NOD mice treated with $1\times10^6$ allogeneic Balb/c MSCs (top panel; n=10), but no reversal of diabetes in newly diabetic NOD mice treated with PBS (bottom panel; n=6) i.v. twice a week for 4 weeks as indicated by the black arrowheads (PBS treated mice were also administered insulin s.c. daily). The blood glucose over time for individual mice was monitored and plotted to assess reversal of disease. Each line represents data from an individual mouse. The solid lines in the top panel represent mice that responded to MSC treatment, whereas the dotted lines signify mice treated with MSCs but did not respond. The horizontal line in both panels represents the blood glucose value at 250 mg/dL. The average blood glucose value of responder mice dropped from 327±83 mg/dL at the time of enrollment to 216±58 mg/dL at the end of the study and was substantially lower than MSC treated mice that did not respond (465±36.8 mg/dL). The high blood glucose values of mice not responding to MSC treatment suggests that the likelihood of these mice having residual beta cell function or the ability to respond to therapy was low. Furthermore, a blood glucose value >350 mg/dL at enrollment did not correlate with whether the animal responded to MSC treatment.

Figure 13B:
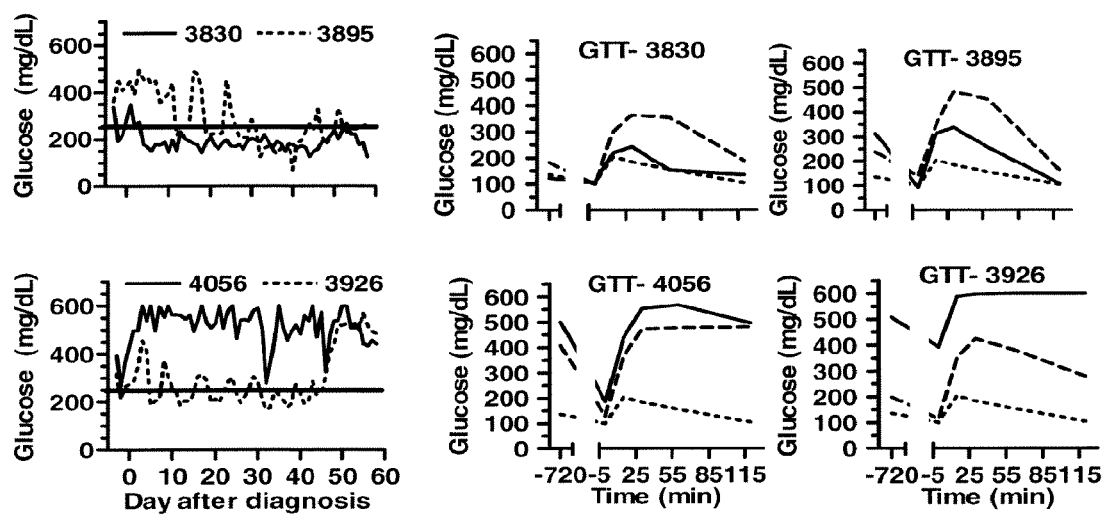
FIG. 13B is a graphical representation of experiments demonstrating the reversal of diabetes as indicated by glucose tolerance tests of MSC-treated mice that did reverse (top graphs, mice 3830 and 3895) compared to MSC-treated mice that did not reverse (bottom graphs, mice 4056 and 3926).

To further assess residual beta cell function in MSC-treated mice, glucose tolerance tests were performed. The response to glucose challenge of MSC treated mice that reversed was abnormal at 7 days but much improved at 33 days post the last MSC dose and similar to the response of non-diabetic NOD mice, showing that residual beta cell function was intact (FIG. 13 B). FIG. 13B shows glucose tolerance tests (GTT) of mice treated with MSCs that responded (top row) or did not respond (bottom row) to MSC treatment. The left panel in the top row depicts the blood glucose values over time for mice 3830 and 3895 that reversed with MSC treatment, whereas the left panel in the bottom row shows the blood glucose values for mice 4056 and 3926 that were treated with MSCs but did not reverse. The middle and right panels show the response of mice 3830, 3895, 4056, and 3926 to glucose challenge 7 days (dashed line) and 33 days (solid line) after the last MSC dose in comparison to a non-diabetic NOD mouse (dotted line). The glucose tolerance test accurately reflected beta cell function in these mice because mouse 4056 never reversed with MSC treatment and responded abnormally to glucose challenge, whereas mouse 3926 responded better when the mouse was showing signs of reversal (day 7), but worse when the mouse was overtly diabetic (day 33).

Figure 13C:
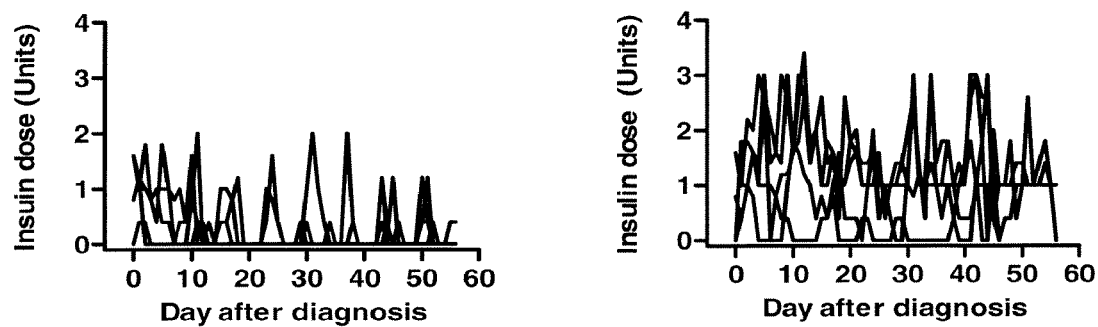
FIG. 13C is a graphical representation of experiments demonstrating the daily insulin dosage for mice treated with MSCs that reversed (left panel) versus MSC treated mice that did not reverse (right panel).

Further supporting these findings is the observation that responder mice required fewer insulin treatments than MSC treated mice that did not reverse (FIG. 13C). FIG. 13C shows the daily insulin dosage for mice treated with MSCs that reversed (left panel), as compared to MSC treated mice that did not reverse (right panel). Each line represents data from an individual mouse. This data shows that mice responding to MSC treatment exhibited improved glucose tolerance and demonstrate the presence of residual beta cell function.

Together, this data shows that MSC treatment alters diabetes development in NOD mice. MSC treatment delays diabetes onset in pre-diabetic mice and reverses hyperglycemia in newly diabetic animals. Those diabetic mice that responded to MSC treatment showed improved responses to glucose challenge and required few insulin treatments, indicating that residual beta cell function was intact in these animals. The observation that MSCs alter diabetes development when administered early in disease shows that MSCs may provide an effective alternative strategy for recently diagnosed type I diabetes patients.

While MSCs modulate disease in both NOD prevention and reversal models, they appear to be more efficacious in reversing disease because half of the MSC treated mice were reversed 30 days after the last MSC dose whereas all the pre-diabetic MSC treated mice eventually succumbed to disease within 4 weeks after the last MSC treatment. While not wishing to be limited to a single theory of the mechanism of action, this difference could be due to the fact that MSCs are most effective at suppressing T cell responses when the response is robust, as in a recently diabetic mouse. The active disease environment might also favor MSC homing to the right tissues as shown by the presence of MSCs in the PLN from all the diabetic mice tested thus far.

Control of glycemia in MSC treated mice indicates that beta cells are functioning in the reversed mice even though insulin staining in the pancreas of these mice was undetected. The lack of detectable insulin staining might be due to constant degranulation of the residual beta cells or because conventional methods used to stain for insulin were inadequate at detecting low insulin amounts (Sherry, et al., *Diabetes* 55:3238-45 v). Insulin staining might have been detected if pancreata were harvested within 3 weeks of enrollment and treatment initiation and not at the end of the study, as shown for newly diabetic mice reversed with anti-CD3. Regardless, MSC therapy alone improved diabetes as indicated by the control of hyperglycemia in over 50% of the treated mice. This important observation demonstrates that MSC therapy for diabetes would be most effective during the beginning phase of disease (new onset). MSC therapy would control ongoing autoimmunity at a time when sufficient numbers of functioning beta cells are still present to restore normal glycemic levels (Keymeulen, et al., *N. Engl. J. Med.* 352: 2598-608 (2005)).

The mechanism(s) by which MSCs lead to reversal are unknown. The data suggests that MSCs dampen the autoimmunity, blunt inflammation, and provide support for residual beta cells. While not wishing to be bound by a single theory of operability, the observations that MSCs, but not other non-mesenchymal cells such as HUVECs, suppress T cell proliferation and blunt TNFα, suggest that MSCs inhibit autoreactive T cell responses and reduce on-going inflammation. Accordingly, MSCs may sense the inflammatory environment and elicit an anti-inflammatory response, including INFα down-modulation.

The data also shows that MSCs preferentially home to the spleen and PLN where MSCs might inhibit autoreactive T cell responses before the T cells migrate to the pancreas. In vitro and in vivo data suggests that MSCs do not effect initial T cell priming but induce hyporesponsiveness of activated T cells (Glennie, et al., *Blood* 105:2821-26 (2005); and Augello, et al., *Arthritis Rheum.* 56:1175-86 (2007)) and exert immune regulatory effects in clinical therapeutic treatment of GvHD (Ringden, et al., *Transplantation* 81:1390-97 (2006); Dean, et al., *Curr. Hematol. Rep.* 2:287-94 (2003)). MSCs might also be inhibiting on-going immune responses in the pancreas itself since MSCs were detected in the pancreas but not other major organs. This data suggests that MSCs have an intrinsic ability to home to areas of inflammation where they may suppress T cell responses at these sites.

The durability of reversal with MSC treatment is important to effective clinical treatment. The data here shows that responder mice remain reversed for 30 days after the last MSC treatment. MSCs have not been detected in vivo 2 weeks after injection, presumably due to normal clearing, suggesting that MSCs are having long lasting effects on the immune response. This characteristic along with the observation that MSCs modulate immune responses locally after homing to sites of injury and inflammation make these cells ideal for treating diabetes and other autoimmune diseases. The data indicates that MSC delivery to new onset T1D patients would control their glycemia and consequently, their daily insulin, making MSC therapy attractive for type I diabetes patients.

Cell therapy to treat autoimmune diseases has increased over the years with the use of BM transplantation and more recently transplantation of mobilized hematopoietic stem cells. The idea is to first ablate then re-set the immune system in these patients. Although data is promising, these procedures are very invasive and autoimmunity recurs (for review see Tyndall, et al., *Arthritis Rheum* 55:521-25 (2006); Burt, et al., *JAMA* 299:925-36 (2008)). As shown by the foregoing experiments, autologous or allogeneic MSC therapy is a more manageable alternative to these other cell therapies.

Equivalents

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

The invention claimed is:

1. A method of treating new onset type 1 diabetes (T1D) in a subject comprising administering isolated autologous or allogeneic mesenchymal stem cells to the subject within six months of diagnosis of new onset T1D, wherein the isolated autologous or allogeneic mesenchymal stem cells are chosen from isolated autologous or allogeneic mesenchymal stem cells expressing an exogenous programmed death ligand and isolated autologous or allogeneic mesenchymal stem cells overexpressing an endogenous programmed death ligand, and wherein the programmed death ligand is chosen from PD-L1 or PD-L2.

2. The method of claim 1, wherein the programmed death ligand is PD-L1.

3. The method of claim 1, wherein the programmed death ligand is PD-L2.

4. A method of treating new onset type 1 diabetes (T1D) in a human subject comprising:
   identifying a subject comprising pancreatic islet beta cells and T cells autoreactive against the pancreatic islet beta cells (beta-cell-autoreactive T cells), wherein the subject received a diagnosis of new onset type 1 diabetes (T1D) within the previous six months; and
   exerting an immunosuppressive effect on the beta-cell-autoreactive T cells in the subject, wherein:
   the exerting of the immunosuppressive effect comprises administering isolated autologous or allogeneic mesenchymal stem cells to the subject within six months of new onset type 1 diabetes (T1D) diagnosis.

5. The method of claim 4, wherein the mesenchymal stem cells are administered within 24 hours of T1D diagnosis.

6. The method of claim 4, wherein the exerting of the immunosuppressive effect further comprises a second administration of autologous or allogeneic mesenchymal stem cells within ten days of the first administration of autologous or allogeneic mesenchymal stem cells.

7. The method of claim 4, wherein the exerting of the immunosuppressive effect further comprises a second administration of autologous or allogeneic mesenchymal stem cells within six months of the first administration of autologous or allogeneic mesenchymal stem cells.

8. The method of claim 4, wherein the mesenchymal stem cells are derived from bone marrow or peripheral blood.

9. The method of claim 4, wherein the mesenchymal stem cells are derived from a population of cells selected from the group consisting of umbilical cord blood cells, muscle cells, fat cells, embryonic yolk sac cells, placenta cells, fetal blood cells, fetal skin cells, and adult skin cells.

10. The method of claim 4, wherein the mesenchymal stem cells are administered to a subject having an abnormally low, but measurable, serum C-peptide level.

11. The method of claim 10, wherein the subject has a stimulated C-peptide test integrated C-peptide level of 1.0 nmol/L or less.

12. The method of claim 11, wherein the subject has a measurable increase in stimulated C-peptide test integrated C-peptide level of 0.54 nmol/L or less.

13. The method of claim 4, wherein the subject has a detectable level of pancreatic autoantibody.

14. The method of claim 4, wherein the mesenchymal stem cells are allogeneic.

15. The method of claim 4, further comprising administering to the subject an immunosuppressive agent.

16. The method of claim 15, wherein the immunosuppressive agent is selected from the group consisting of prednisone, azathioprine, cyclosporine, antibodies against CD3, antibodies against CD20, and antithymocyte globulin.

17. The method of claim 4, further comprising administering to the subject a peptide vaccine.

18. The method of claim 17, wherein the vaccine induces tolerance of insulin-producing cells.

19. The method of claim 18, wherein the vaccine comprises an autoimmune Type I diabetes (T1D) autoantigen.

20. The method of claim 19, wherein the vaccine comprises an islet-cell autoantigen selected from the group consisting of insulin, proinsulin, glutamic acid decarboxylase (GAD65), HSP60, and IA-2 protein tyrosine phosphatase.

21. The method of claim 4, further comprising administering a non-mitogenic anti-CD3 active compound selected from the group consisting of CD3 antibodies and fragments of CD3 antibodies.

22. The method of claim 21, wherein the non-mitogenic anti-CD3 active compound is administered in an injectable form comprising 5 to 20 mg of the non-mitogenic anti-CD3 active compound.

* * * * *